United States Patent
Sheppard et al.

(10) Patent No.: US 6,544,946 B1
(45) Date of Patent: Apr. 8, 2003

(54) INHIBITORS FOR USE IN HEMOSTASIS AND IMMUNE FUNCTION

(75) Inventors: Paul O. Sheppard, Granite Falls, WA (US); Gerald W. Lasser, Lynnwood, WA (US); Paul D. Bishop, Fall City, WA (US)

(73) Assignee: ZymoGenetics, Inc., Seattle, WA (US)

( * ) Notice: Subject to any disclaimer, the term of this patent is extended or adjusted under 35 U.S.C. 154(b) by 102 days.

(21) Appl. No.: 09/619,740

(22) Filed: Jul. 19, 2000

Related U.S. Application Data

(63) Continuation-in-part of application No. 09/506,855, filed on Feb. 17, 2000, now Pat. No. 6,448,221, which is a continuation-in-part of application No. 09/444,794, filed on Nov. 22, 1999, now abandoned, which is a continuation-in-part of application No. 09/253,604, filed on Feb. 19, 1999, now abandoned.

(51) Int. Cl.$^7$ .......................... A61K 38/00; C07K 1/00; C07K 14/00
(52) U.S. Cl. ............................. 514/2; 514/12; 514/929; 514/4; 424/569; 424/574; 530/350
(58) Field of Search .......................... 514/2, 4, 12, 929; 424/569, 574; 530/350

(56) References Cited

U.S. PATENT DOCUMENTS

| | | | | |
|---|---|---|---|---|
| 5,811,442 A | * | 9/1998 | Bencherif et al. | 514/384 |
| 6,265,544 B1 | * | 7/2001 | Sheppard | 435/320.1 |

FOREIGN PATENT DOCUMENTS

| | | |
|---|---|---|
| WO | 96/39429 | 12/1996 |
| WO | 99/02546 | 1/1999 |
| WO | 99/04000 | 1/1999 |
| WO | 99/06551 | 2/1999 |
| WO | 99/10492 | 3/1999 |
| WO | PCT/JP98/04862 | 5/1999 |
| WO | 99/21577 | 5/1999 |
| WO | 99/28462 | 6/1999 |
| WO | 99/33979 | 7/1999 |
| WO | 99/38973 | 8/1999 |
| WO | 99/55865 | 11/1999 |
| WO | 99/59618 | 11/1999 |

OTHER PUBLICATIONS

Maeda et al., *Biochem. & Biophys. Research Communications*. 221: 286–289. 1996.
Nakano et al., *J. Biochem*. 120: 803–812. 1996.
Scherer et al., *J. of Biological Chemistry*. 270: 26746–26749. 1995.
Shapiro et al., *Current Biology*. 8: 335–338. 1998.
Okamoto et al., *Horm Metab Res*. 32: 47–50. 2000.
Ouchi et al., *Circulation*. 103: 1057–1063. 2001.
Yokota et al., *Blood*. 96: 1723–1732. 2000.
Golino et al., *Thrombosis and Haemostasis*. 67: 302–305. 1992.
Fruebis et al., *PNAS*. 98: 2005–2010. 2001.
Ouchi et al., *Circulation*. 100: 2473–2476. 1999.
Acton et al., *Journal of Biological Chemistry*. 268: 3530–3537. 1993.
Buerke et al., *Journal of Pharmacology and Experimental Therapeutics*. 286: 429–438. 1998.
Deckmyn et al., *Blood*. 85: 712–719. 1995.
Harsfalvi et al., *Blood*. 85: 705–711. 1995.
Keller et al., *Journal of Biological Chemistry*. 268: 5450–5456. 1993.
Noeske–Jungblut et al., *Journal of Biological Chemistry*. 269: 5050–5053. 1994.
Rossen et al., *Circulation Research*. 62: 572–584. 1988.
Rubin et al., *Ann. Vasc. Surg*. 7: 200–207. 1993.
Barnes et al., *Current Opinion in Hematology*. 5:314–320. 1998.
Waxman et al., *Journal of Biological Chemistry*. 268:5445–5449. 1993.

\* cited by examiner

*Primary Examiner*—Jeffrey Stucker
*Assistant Examiner*—Jegatheesan Seharaseyon
(74) *Attorney, Agent, or Firm*—Brian J. Walsh; Phillip B. C. Jones

(57) ABSTRACT

The present invention relates to polynucleotide and polypeptide molecules for use as inhibitors in hemostasis and immune function. Such inhibitors are members of the family of proteins bearing a collagen-like domain and a globular domain. The inhibitors are useful for promoting blood flow in the vasculature by reducing thrombogenic and complement activity. The inhibitors are also useful for pacifying collagenous surfaces and modulating wound healing.

21 Claims, 8 Drawing Sheets

```
zsig37_3_z   MGSRGQGLLLAYCLLLAFASG------------------------ :  21
HUMUPST2_1   MLLLGAVLLLLALP-------------------------------- :  14
C1QA_HUMAN   MEGPRGWLVLCVLAISLA---------------------------- :  18
HP25_TAMAS   MPAQRGGALSMGAAGFWILVLSITSALA------------------ :  28
HP27_TAMAS   MYEAGKRASFMGGAGIWILALSVLMHVVCS---------------- :  30
CERL_RAT     MPAPGRGPRGPLLSMPGRRGALREPADFGSSLGAALALLLLLLPACC :  47 zsig37_3_z   -----LVLSRVPHVQGEQQEWEGTEELPSPPDHAERAEEQHEKYRPS :  63
HUMUPST2_1   -----GHDQ---------------ETTTQGP----------GVLLPL :  31
C1QA_HUMAN   -----SMVT---------------EDLCRAPD------------GK :  32
HP25_TAMAS   -----DSNNQGNSEPC------------------------------ :  39
HP27_TAMAS   -------ETQGNPESC------------------------------ :  39
CERL_RAT     PVKA-QNDTEPIVLEGKC----LVVCDSSPSGDGAVTSSL------- :  82 zsig37_3_z   QDQGLPASRCLRCCDPGTSMYPATAVPQINITILKGEKGDRGDRGLQ : 110
HUMUPST2_1   PKGACTGWMAGIPGHPGHNGAPGRDG-RDGTPGEKGEKGDPGLIGPK :  77
C1QA_HUMAN   KGEAGRPGRRGRPGLKGEQGEPGAPGIRTGIQGLKGDQGEPGPSGNP :  79
HP25_TAMAS   ----------------------------------GPPGPPGPPGIP :  51
HP27_TAMAS   ----------------------------------NVPGPQGPPGMR :  51
CERL_RAT     ----------------------- ---------------------- :  82 zsig37_3_z   GKYGKTGSAGARGHTGPKGQKGSMGAPGE--RCK-SHYAAFSVGRKK : 154
HUMUPST2_1   GDIGETGVPGAEGPRGFPGIQGRKGEPGE--GAY-VYRSAFSVGLET : 121
C1QA_HUMAN   GKVGYPGPSGPLGARGIPGIKGTKGSPGN--IKD-QPRPAFSAIRRN : 123
HP25_TAMAS   GFPGAPGALGPPGPPGPVPGIPGPQGPPGDVEKCSSRPKSAFAVKLSE :  98
HP27_TAMAS   GPPGTPGKPGPPGWNGFPGLPGPPGPPGMTVNCHSKGTSAFAVKANE :  98
CERL_RAT     --------------------GISVRSG----SAKVAFSATRSTNHE : 104 zsig37_3_z   PMHSNHYYQTVIFDTEFVNLYDHFNMFTGKFYCYVPGLYFFSLNV-H : 200
HUMUPST2_1   YVTI--PNMPIRFTKIFYNQQNHYDGSTGKFHCNIPGLYYFAYHI-T : 165
C1QA_HUMAN   PPMG---GNVVIFDTVITNQEEPYQNHSGRFVCTVPGYYYFTFQV-L : 166
HP25_TAMAS   RPPE--PFQPIVFKEALYNQEGHFNMATGEFSCVLPGVYNFGFDIRL : 143
HP27_TAMAS   LPPA--PSQPVIFKEALHDAQGHFDLATGVFTCPVPGLYQFGFHIEA : 143
CERL_RAT     PSEMSNRTMTIYFDQVLVNIGNHFDLASSIFVAPRKGIYSFSFHVVK : 151 zsig37_3_z   T---WNQKETYLHIMKNEEEVVILFAQVGDRSIMQSQS--LMLELRE : 242
HUMUPST2_1   V----YMKDVKVSLFKKDKAMLFTYDQYQENNVDQASG-SVLLHLEV : 207
C1QA_HUMAN   SQ--WEICLSIVSSSRGQVRRSLGFCDTTNKGLFQVVSGGMVLQLQQ : 211
HP25_TAMAS   FQ--SSVKIRLMRDGI-QVREK----EAQANDSYKHAMGSVIMALGK : 183
HP27_TAMAS   VQ--RAVKVSLMRNGT-QVMER----EAEAQDGYEHISGTAILQLGM : 183
CERL_RAT     VYNRQTIQVSLMQNGY-PVISA----FAGDQDVTREAASNGVLLL-M : 192
```

Fig. 1A

```
zsig37_3_z  QDQVWVRLYKG-ERENAIFSEELDTYITFSGYLVKHATEP : 281
HUMUPST2_1  GDQVWLQVYGEGERNGLYADNDNDS--TFTGFLLYHDTN- : 244
C1QA_HUMAN  GDQVWVEKDP--KKGHIYQGSEADS--VFSGFLIFPSA-- : 245
HP25_TAMAS  GDKVWLESKL--KGTESEKGI-THI--VFFGYLLYGK--- : 215
HP27_TAMAS  EDRVWLENKL--SQTDLERGT-VQA--VFSGFLIHEN--- : 215
CERL_RAT    EREDKVHLKL--ERGNLMGGW-KYS--TFSGFLVFPL--- : 224
```

Fig. 1B

|  | zsig37 | HUMUPST2_1 | C1QA_HUMAN | HP25_TAMAS | HP27_TAMAS | CERL_RAT |
|---|---|---|---|---|---|---|
| zsig37 | 100 | | | | | |
| HUMUPST2_1 | 32 | 100 | | | | |
| C1QA_HUMAN | 30 | 33 | 100 | | | |
| HP25_TAMAS | 31 | 31 | 32 | 100 | | |
| HP27_TAMAS | 28 | 29 | 32 | 53 | 100 | |
| CERL_RAT | 21 | 25 | 24 | 27 | 33 | 100 |

Fig. 2

INHIBITORS FOR USE IN HEMOSTASIS AND IMMUNE FUNCTION

REFERENCE TO RELATED APPLICATIONS

This application is a continuation-in-pan of U.S. patent application Ser. No. 09/506,855 (filed on Feb. 17, 2000), now U.S. Pat. No. 6,448,221, which is a continuation-in-part of U.S. patent application Ser. No. 09/444,794 (filed on Nov. 22, 1999), now abandoned, which is a continuation-in-part of U.S. patent application Ser. No. 09/253,604 (filed on Feb. 19, 1999), now abandoned.

BACKGROUND OF THE INVENTION

Injury to the blood vessels sets in motion a series of events to repair the damage and control release of blood from the vessel. This process is known as hemostasis. Platelets play an early role in hemostasis by forming a thrombus or plug to temporarily repair the vessel damage. Platelets normally do not interact with the endothelium lining the vessel walls, but injury to blood vessels, through accident or during surgical procedures, may disrupt endothelial cells. Depending on the extent of the injury, various subendothelial elements such as collagens, elastic lamina or smooth muscle cells with associated fibrillar collagens will be exposed to the flowing blood.

When the subendothelium is exposed following vessel injury, platelets moving in the local blood flow interact with exposed subendothelium matrix containing collagen and are slowed down. Further interaction between receptors on the platelet surface and the exposed collagen layer leads to platelet binding and activation resulting in the arrest of local blood flow. The bound platelets are activated and form aggregates with platelets in the passing blood flow through the formation of fibrinogen-interplatelet bridges (Moroi. and Jung, *Frontiers in Bioscience* 3:719–28, 1998; Barnes et al., *Atherosclerosis XI*, Jacotot et al., eds., Elsevier Science, pp. 299–306, 1998 and Barnes et al., *Curr. Opin. Hematol.* 5:314–20, 1998).

The hemostatic response is graded and dependent on the degree of injury to the blood vessel, the specific blood vessels constituents exposed and the blood flow conditions in the injured area (Rand et al., *Thrombosis and Haemostasis* 78:445–50, 1997). Exposure of the subendothelium matrix (type VI collagen and von Willebrand factor), such as during mild vascular injury, promotes a low degree of adhesion and aggregation in areas with low blood flow conditions. Injuries that result in a greater degree of vascular trauma and exposure of additional vascular constituents, such as the internal elastic lamina and elastin-associated microfibrils, will stimulate the formation of stronger platelet aggregates. Severe vascular trauma, exposing fibril collagens, provokes a thrombotic platelet response, which protects the victim from excessive loss of blood (Rand et al., ibid.).

Inhibitors of hemostasis would be useful for to increase blood flow following vascular injury and to pacify collagenous surfaces.

Complement factor C1q consists of six copies of three related polypeptides (A, B and C chains), with each polypeptide being about 225 amino acids long with a near amino-terminal collagen domain and a carboxy-terminal globular region. Six triple helical regions are formed by the collagen domains of the six A, six B and six C chains, forming a central region and six stalks. A globular head portion is formed by association of the globular carboxy terminal domain of an A, a B and a C chain. C1q is therefore composed of six globular heads linked via six collagen-like stalks to a central fibril region. Sellar et al., *Biochem. J.* 274: 481–90, 1991. This configuration is often referred to as a bouquet of flowers. Acrp30 has a similar bouquet structure formed from a single type of polypeptide chain.

C1q has been found to stimulate defense mechanisms as well as trigger the generation of toxic oxygen species that can cause tissue damage (Tenner, *Behring Inst. Mitt.* 93:241–53, 1993). C1q binding sites are found on platelets. Additionally complement and C1q play a role in inflammation. The complement activation is initiated by binding of C1q to immunoglobulins Inhibitors of C1q and the complement pathway would be useful for anti-inflammatory applications, inhibition of complement activation and thrombotic activity.

The present invention provides such polypeptides for these and other uses that should be apparent to those skilled in the art from the teachings herein.

SUMMARY OF THE INVENTION

Within one aspect the invention provides a method of promoting blood flow within the vasculature of a mammal comprising administering to said mammal a therapeutically effective amount of an adipocyte complement related protein; in a pharmaceutically acceptable vehicle; whereby said adipocyte complement related protein reduces thrombogenic and complement activity within said vasculature. Within one embodiment the adipocyte complement related protein comprises a polypeptide comprising a sequence of amino acid residues that is at least 75% identical in amino acid sequence to residues 26–281 of SEQ ID NO:2, wherein said sequence comprises: Gly-Xaa-Xaa or Gly-Xaa-Pro repeats forming a collagen domain, wherein Xaa is any amino acid, and a carboxy-terminal globular portion. Within a related embodiment the polypeptide comprises a sequence of amino acid residues that is at least 90% identical in amino acid sequence to residues 22–281 of SEQ ID NO:2. Within another embodiment the polypeptide comprises an amino acid sequence that is at least 90% identical in amino acid sequence to residues 26–281 of SEQ ID NO:2. Within yet another embodiment any differences between said polypeptide and SEQ ID NO:2 are due to conservative amino acid substitutions. Within another embodiment the collagen domain consists of 13 Gly-Xaa-Xaa repeats and 1 Gly-Xaa-Pro repeat. Within yet another embodiment the globular domain consists of ten beta sheets. Within a related embodiment the beta sheets are associated with amino acid residues corresponding to 147–151, 170–172, 178–181, 191–203, 207–214, 219–225, 227–239, 244–250, and 269–274 of SEQ ID NO:2. Within yet another embodiment the polypeptide comprises residues 1–281 of SEQ ID NO:2 or residues 1–281 of SEQ ID NO:44.

The invention also provided the polypeptide is complexed to a second polypeptide to form a oligomer. Within one embodiment the polypeptides are complexed by intermolecular disulfide bonds. Within another embodiment the oligomer is a trimer. Within yet another embodiment the oligomer is a hexamer. Within yet another embodiment the oligomer is an 18 mer.

Within another embodiment the polypeptide reduces thrombogenic and complement activity by inhibition of the complement pathway and inhibition collagen-mediated platelet adhesion, activation or aggregation. Within another embodiment polypeptide is administered prior to, during or following an acute vascular injury in said mammal. Within yet another embodiment the injury is due to vascular reconstruction. Within a related embodiment the vascular reconstruction comprises angioplasty, coronary artery bypass graft, endarterectomy, microvascular repair or anastomosis of a vascular graft. Within another related embodiment the injury is due to trauma, stroke or aneurysm.

Within another aspect the invention provides a method of pacifying damaged collagenous tissues within a mammal comprising administering to said mammal a therapeutically effective amount of an adipocyte complement related protein; whereby said protein renders the damaged collagenous tissue inert towards complement activation, thrombotic activity or immune activation. Within one embodiment the damaged collagenous tissues are due to injury associated with ischemia and reperfusion. Withnin another embodiment the injury comprises trauma injury ischemia, intestinal strangulation, or injury associated with pre- and post-establishment of blood flow. Within yet another embodiment the polypeptide is administered, to a mammal suffering from cardiopulmonary bypass ischemia and recesitation, myocardial infarction, or post-trauma vasospasm. Within a related embodiment the post-trauma vasospasm comprises stroke, percutanious transluminal angioplasty, endarterectomy, accidental vascular trauma or surgical-induced vascular trauma.

Within yet another aspect the invention provides a method of pacifying the surface of a prosthetic biomaterial for use in association with a mammal comprising administering to said mammal a therapeutically effective amount of an adipocyte complement related protein; whereby said polypeptide renders the surface of said prosthetic biomaterial inert towards complement activation, thrombotic activity or immune activation. Within one embodiment the surface of said prosthetic biomaterial is coated with collagen or collagen fragments, gelatin, fibrin or fibronectin.

Within another aspect of the invention is provided a method of mediating wound repair within a mammal comprising administering to said mammal a therapeutically effective amount of an adipocyte complement related protein; whereby said polypeptide enhances progression in wound healing.

BRIEF DESCRIPTION OF THE DRAWINGS

FIG. 1 illustrates a multiple alignment of and zsig37 polypeptide of the present invention and HUMUPST2_1 (Maeda et al., *Biochem. Biophys. Res. Comm.* 221(2): 286–9, 1996) (SEQ ID NO:51); C1QA_HUMAN (Sellar et al., *Biochem. J.* 274: 481–90, 1991, Reid, *Biochem. J.* 179: 367–71, 1979, and Reid et al., *Biochem. J.* 203: 559–69, 1982) (SEQ ID NO:52); HP25_TAMAS (Takamatsu et al., *Mol. Cell. Biol.* 13: 1516–21, 1993 and Kondo & Kondo, *J. Biol. Chem.* 267: 473–8, 1992) (SEQ ID NO:53); HP27_TAMAS (Takamatsu et al. and Kondo & Kondo referenced above) (SEQ ID NO:54); and CERL_RAT (Wada & Ohtani, *Brain Res. Mol. Brain Res.* 9: 71–7, 1991) (SEQ ID NO:55).

FIG. 2 is a matrix showing percent amino acid identity in a comparison of the six proteins shown in the multiple alignment FIG. 1.

DETAILED DESCRIPTION OF THE INVENTION

Figure 3A:
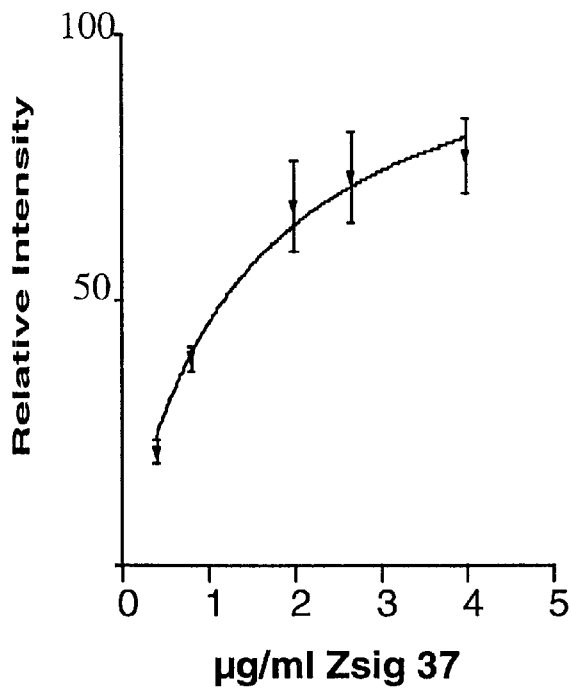
FIG. 3a shows zsig37-FITC binding to type VI collagen.

Prior to setting forth the invention in detail, it may be helpful to the understanding thereof to define the following terms.

The term "affinity tag" is used herein to denote a peptide segment that can be attached to a polypeptide to provide for purification or detection of the polypeptide or provide sites for attachment of the polypeptide to a substrate. In principal, any peptide or.protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), substance P, Flag™ peptide (Hopp et al., *Biotechnology* 6:1204–10, 1988; available from Eastman Kodak Co., New Haven, Conn.), streptavidin binding peptide, or other antigenic epitope or binding domain. See, in general Ford et al., *Protein Expression and Purification* 2: 95–107, 1991. DNAs encoding affinity tags are available from commercial suppliers (e.g., Pharmacia Biotech, Piscataway, N.J.).

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "degenerate nudleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "ortholog" denotes a polypeptide or protein obtained from one species that is the functional counterpart of a polypeptide or protein from a different species. Sequence differences among orthologs are the result of speciation.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, OR, and Amersham Corp., Arlington Heights, Ill., using techniques that are well known in the art.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention was based in part upon the discovery that a novel adipocyte complement related protein homolog inhibits collagen-mediated platelet activation and the complement pathway including C1q. This protein was designated zsig37 and is fully described in the commonly assigned published PCT patent application WO 99/04000.

The zsig37 nucleotide sequence (SEQ ID NO:1) encodes a polypeptide (SEQ ID NO:2) having an amino-terminal signal sequence, an adjacent N-terminal region of non-homology, a truncated collagen domain composed of Gly-Xaa-Xaa or Gly-Xaa-Pro repeats and a carboxy-terminal globular portion. The novel polynucleotide sequence also contains a long 3' untranslated region. The general polypeptide structure set forth above is shared by Acrp30 and HUMUPST2_1, except that the collagen-like domain of each of those proteins is longer than that of zsig37 polypeptides. Also, the HUMUPST2_1 DNA sequence is characterized by a long 3' untranslated region. Moreover, Acrp30 and all of the sequences aligned in FIG. 1, with the exception of CERL_RAT, share a conserved cysteine residue at position 187 of zsig37 polypeptide as shown in FIG. 1 and SEQ ID NO: 2. Also, the zsig37 polypeptides of the present invention include a putative N-linked glycosylation site at amino acid 93 (Asn) of SEQ ID NO: 2.

Analysis of the tissue distribution of the mRNA corresponding to zsig37 showed that expression was highest in heart and placenta, with relatively less intense signals in kidney, ovary, adrenal gland and skeletal muscle and lower signals in a wide variety of other tissues present on the Northern blot.

A homolog relationship with adipocyte complement related protein Acrp30 (SEQ ID NO: 3) and adipocyte secreted protein apM1 (HUMUPST2_1 in FIGS. 1 and 2) (SEQ ID NO:51) was established for zsig37. Somewhat more distant homology was also identified to complement component C1Q A chain (SEQ ID NO:52), two factors observed in the active state of hibernating Siberian woodchucks (HP25_TAMAS (SEQ ID NO:53) and HP27_TAMAS (SEQ ID NO:54)) and a rat brain protein (CERL_RAT) (SEQ ID NO:55), as shown in FIGS. 1 and 2.

The nucleotide sequence of zsig37 is described in SEQ ID NO: 1, and its deduced amino acid sequence is described in SEQ ID NO: 2. A degenerate nucleotide sequence encoding the polypeptide of SEQ ID NO:2 is provided in SEQ ID NO:23. As described generally above, the zsig37 polypeptide includes a signal sequence, ranging from amino acid 1 (Met) to amino acid residue 21 (Gly). An alternative signal sequence ranges from amino acid 1 (Met) to amino acid 25 (Ser). The mature polypeptide therefore ranges from amino acid 22 (Leu) or 26 (Arg) to amino acid 281 (Pro). Within the mature polypeptide, an N-terminal region of no known homology is found, ranging between amino acid residue 22 (Leu) and 98 (Lys). In addition, a truncated collagen domain is found between amino acid 99 (Gly) and 140 (Arg). In the truncated collagen domain, 1 perfect Gly-Xaa-Pro and 13 imperfect Gly-Xaa-Xaa repeats are observed. In contrast, Acrp30 contains 22 perfect or imperfect repeats. The zsig37 polypeptide also includes a carboxy-terminal globular domain, ranging from about amino acid 141 (Cys) to 281 (Pro). Zsig37 polypeptide, HUMUPST2_1 and Acrp30 appear to be homologous within the collagen domain and in the globular domain, but not in the N-terminal portion of the mature polypeptide.

The globular C1q domain of ACRP30 has been determined to have a 10 beta strand "jelly roll" topology (Shapiro and Scherer, *Curr. Biol.* 8:335–8, 1998) that shows significant structural homology to the TNF family and the zsig37 sequence as represented by SEQ ID NO:2 contains all 10 beta-strands of this structure (amino acid residues 147–151, 170–172, 178–181, 185–188, 191–203, 207–214, 219–225, 227–238, 244–250, and 269–274 of SEQ ID NO:2). These strands have been designated "A", "A'", "B", "B'", "C", "D", "E", "F", "G" and "H" respectively.

Zsig37 has two receptor binding loops, at amino acid residues 152–180 and 213–226. Amino acid residues 191 (Gly), 193 (Tyr), 238 (Leu) and 272 (Gly) appear to be conserved across the superfamily including CD40, TNFα, TNFβ, ACRP30 and zsig37.

Another aspect of the present invention includes use of zsig37 polypeptide fragments as inhibitors of hemostasis and immune functions. Preferred fragments include the collagen-like domain of zsig37 polypeptides, ranging from amino acid 99 (Gly) to amino acid 140 (Arg) of SEQ ID NO:2, a portion of the zsig37 polypeptide containing the collagen-like domain or a portion of the collagen-like domain capable of dimerization or oligomerization. Other preferred fragments include the globular domain of zsig37 polypeptides, ranging from amino acid 140 (Arg) or 141 (Cys) to 281 (Pro) of SEQ ID NO: 2, a portion of the zsig37 polypeptide containing the globular-like domain or an active portion of the globular-like domain. Another zsig37 polypeptide fragment of the present invention include both the collagen-like domain and the globular domain ranging from amino acid residue 99 (Gly) to 281 (Pro) of SEQ ID NO: 2. These fragments are particularly useful in the inhibition of collagen-mediated platelet activation and inhibition of complement and C1q.

The present invention also provides use of zsig37 fusion proteins. For example, fusion proteins of the present invention encompass (1) a polypeptide selected from the group comprising: (a) polypeptide molecules comprising a sequence of amino acid residues as shown in SEQ ID NO: 2 from amino acid residue 1 (Met), 22 (Leu) or 26 (Arg) to amino acid residue 281 (Pro); (b) polypeptide molecules ranging from amino acid 99 (Gly) to amino acid 140 (Arg) of SEQ ID NO: 2, a portion of the zsig37 polypeptide containing the collagen-like domain or a portion of the collagen-like domain capable of dimerization or oligomerization; (c) polypeptide molecules ranging from amino acid 140 (Arg) or 141 (Cys) to 281 (Pro) of SEQ ID NO: 2, a portion of the zsig37 polypeptide containing the globular-like domain or an active portion of the globular-like domain; or (d) polypeptide molecules ranging from amino acid 99 (Gly) to 281 (Pro), a portion of the zsig37 polypeptide including the collagen-like domain and the globular domain; and (2) another polypeptide. The other polypeptide may be alternative or additional globular domain, an alternative or additional collagen-like domain, a signal peptide to facilitate secretion of the fusion protein or the like.

Also useful within the methods of the invention are zsig37 agonists and antagonists. Methods of identifying antagonists are known in the art. For example, antagonists of the zsig37 polypeptide can be identified by providing cells responsive to a zsig37 polypeptide, culturing a first portion of the cells in the presence of zsig37 polypeptide, culturing a second portion of the cells in the presence of the zsig37 polypeptide and a test compound, and detecting a decrease in a cellular response of the second portion of the cells as compared to the first portion of the cells. In addition to those assays disclosed herein, samples can be tested for inhibition of zsig37 activity within a variety of assays designed to measure receptor binding or the stimulation/inhibition of zsig37-dependent cellular responses. For example, zsig37-responsive cell lines can be transfected with a reporter gene construct that is responsive to a zsig37-stimulated cellular pathway. Reporter gene constructs of this type are known in the art, and will generally comprise a zsig37-DNA response element operably linked to a gene encoding an assayable protein, such as luciferase. DNA response elements can include, but are not limited to, cyclic AMP response elements (CRE), hormone response elements (HRE), insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6, 1988 and Habener, *Molec. Endocrinol.* 4 (8):1087–94, 1990. Hormone response elements are reviewed in Beato, *Cell* 56:335–44;1989. Candidate compounds, solutions, mixtures or extracts are tested for the ability to inhibit the activity of zsig37 on the target cells as evidenced by a decrease in zsig37 stimulation of reporter gene expression. Assays of this type will detect compounds that directly block zsig37 binding to cell-surface receptors, as well as compounds that block processes in the cellular pathway subsequent to receptor-ligand binding. In the alternative, compounds or other samples can be tested for direct blocking of zsig37 binding to receptor using zsig37 tagged with a detectable label (e.g., $^{125}$I, biotin, horseradish peroxidase, FITC, and the like). Within assays of this type, the ability of a test sample to inhibit the binding of labeled zsig37 to the receptor is indicative of inhibitory activity, which can be confirmed through secondary assays. Receptors used within binding assays may be cellular receptors or isolated, immobilized receptors.

Also useful within the methods of the invention are antibodies that specifically bind to zsig37 polypeptide epitopes, peptides or polypeptides. Methods for preparing polyclonal and monoclonal antibodies are well known in the art (see, for example, Sambrook et al., *Molecular Cloninq: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982).

As would be evident to one of ordinary skill in the art, polyclonal antibodies can be generated from inoculating a variety of warm-blooded animals such as horses, cows, goats, sheep, dogs, chickens, rabbits, mice, hamsters, guinea pigs and rats as well as transgenic animals such as transgenic sheep, cows, goats or pigs. Antibodies may also be expressed in yeast and fungi in modified forms as well as in mammalian and insect cells. The zsig37 polypeptide or a fragment thereof serves as an antigen (immunogen) to inoculate an animal or elicit an immune response. Suitable antigens would include the zsig37 polypeptide encoded by SEQ ID NO:2 from amino acid residue 22–281 of SEQ ID NO:2, from amino acid residue 26–281 of SEQ ID NO:2, or a contiguous 9–281 amino acid residue fragment thereof. The immunogenicity of a zsig37 polypeptide may be increased through the use of an adjuvant, such as alum (aluminum hydroxide) or Freund's complete or incomplete adjuvant. Polypeptides useful for immunization also include fusion polypeptides, such as fusions of zsig37 or a portion thereof with an immunoglobulin polypeptide or with an affinity tag. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to zsig37 protein or peptide, and selection of antibody display libraries in phage or similar vectors (for instance, through use of immobilized or labeled zsig37 protein or peptide).

Antibodies are defined to be specifically binding if: 1) they exhibit a threshold level of binding activity, and/or 2) they do not significantly cross-react with related polypeptide molecules. First, antibodies herein specifically bind if they bind to a zsig37 polypeptide, peptide or epitope with a binding affinity ($K_a$) of $10^6$ mol$^{-1}$ or greater, preferably $10^7$ mol$^{-1}$ or greater, more preferably $10^8$ mol$^{-1}$ or greater, and most preferably $10^9$ mol$^{-1}$ or greater. The binding affinity of an antibody can be readily determined by one of ordinary skill in the art, for example, by Scatchard analysis (Scatchard, *Ann. N.Y. Acad. Sci.* 51: 660–672, 1949).

Second, antibodies specifically bind if they do not significantly cross-react with related polypeptides. Antibodies do not significantly cross-react with related polypeptide molecules, for example, if they detect zsig37 polypeptide but not known related polypeptides using a standard Western blot analysis (Ausubel et al., ibid.). Examples of known related polypeptides include other members of a protein family such as Acrp30 (SEQ ID NO:3), the polypeptides shown in alignment FIG. 1 and the like. They could also include, if desired, orthologs and mutant human zsig37 polypeptides. Moreover, antibodies may be "screened against" known related polypeptides to isolate a population that specifically binds to the inventive polypeptides. For example, antibodies raised to human zsig37 polypeptides are adsorbed to related polypeptides adhered to insoluble matrix; antibodies specific to human zsig37 polypeptides will flow through the matrix under the proper buffer conditions. Such screening allows isolation of polyclonal and monoclonal antibodies non-crossreactive to closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art (see, *Fundamental Immunology*, Paul (eds.), Raven Press, 1993; Getzoff et al., *Adv. in Immunol.* 43: 1–98, 1988; *Monoclonal Antibodies: Principles and Practice*, Goding, J. W. (eds.), *Academic Press Ltd.*, 1996; Benjamin et al., *Ann. Rev. Immunol.* 2: 67–101, 1984). Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay.

The effect of zsig37 polypeptides, fragments, fusions, agonists or antagonists on hemostasis, in particular platelet adhesion and activation leading to platelet aggregation can be determined by using methods and assays provided herein and those known in the art. Collagen is a potent inducer of platelet aggregation. This poses risks to patients recovering from vascular injures. Inhibitors of collagen-induced platelet aggregation would be useful for such purposes. Zsig37 was found to bind to fibronectin and type I, II, III, V and VI collagens. In particular, zsig37 binds to specific domains on collagen VI in a concentration dependent manner. Zsig37 was also found to inhibit collagen-mediated platelet activation. Zsig37-induced inhibition was selective for collagen activation, zsig37 had no effect on platelets activated by known platelet activators ADP or thrombin. These results are described in more detail below in the Example section below. It is anticipated that zsig37 polypeptides, fragments, fusions, agonists or antagonists will be useful for blocking the binding of platelets to collagen-coated surfaces and reducing associated collagen-induced platelet aggregation.

C1q is a component of the complement pathway and has been found to stimulate defense mechanisms as well as trigger the generation of toxic oxygen species that can cause tissue damage (Tenner, *Behring Inst. Mitt.* 93:241–53, 1993). C1q binding sites are found on platelets. C1q, independent of an immune binding partner, has been found to inhibit platelet aggregation but not platelet adhesion or shape change. The amino terminal region of C1q shares homology with collagen (Peerschke and Ghebrehiwet, *J. Immunol.* 145:2984–88, 1990). zsig37 binds to complement C1q in a concentration dependent manner. zsig37 was found to be effective in inhibiting the complement pathway including C1q with both sensitized and unsensitized sheep erythrocytes.

Zsig37 polypeptides, fragments, fusion proteins, antibodies, agonists or antagonists of the present invention can be used in methods for promoting blood flow within the vasculature of a mammal by reducing the number of platelets that adhere and are activated and the size of platelet aggregates. Such methods would comprise administration of a therapeutically effective amount of zsig37 polypeptides, fragments, fusions, antibodies, agonists or antagonists to a mammal in need of such treatment, whereby zsig37 reduces thrombogenic and complement activity within the vasculature of the mammal. As is described below, zsig37 polypeptides inhibit collagen-mediated platelet activation and inactivate fibronectin and type I, II, III, V and VI collagens through binding. Zsig37 administration reduces thrombogenic activity at the site of vascular injury by reducing the modes for platelet adhesion, activation and aggregation. Zsig37 also inhibits the complement pathway and C1q as is described below, thus reducing complement activity within the vasculature. Zsig37 polypeptides, fragments, fusions, antibodies, agonists or antagonists used in such methods can be administered prior to, during or following an acute vascular injury in the mammal.

In a preferred method, the vascular injury is due to vascular reconstruction, including but not limited to, angioplasty, endarterectomy, coronary artery bypass graft, microvascular repair or anastomosis of a vascular graft. Also contemplated are vascular injuries due to trauma, stroke or aneurysm. In other preferred methods the vascular injury is due to plaque rupture, degradation of the vasculature, complications associated with diabetes and atherosclerosis. Plaque rupture in the coronary artery induces heart attack and in the cerebral artery induces stroke. Use of zsig37 polypeptides, fragments, fusion proteins, antibodies, agonists or antagonists in such methods would also be useful for ameliorating whole system diseases of the vasculature associated with the immune system, such as disseminated intravascular coagulation (DIC) and SIDs. Additionally the complement inhibiting activity would be useful for treating non-vasculature immune diseases such as arteriolosclerosis.

A correlation has been found between the presence of C1q in localized ischemic myocardium and the accumulation of leukocytes following coronary occlusion and reperfusion. Release of cellular components following tissue damage triggers complement activation which results in toxic oxygen products that may be the primary cause of myocardial damage (Rossen et al., *Circ. Res.* 62:572–84, 1998 and Tenner, ibid.). Blocking the complement pathway was found to protect ischemic myocardium from reperfusion injury (Buerke et al., *J. Pharm. Exp. Therp.* 286:429–38, 1998).

The complement inhibition and C1q binding activity of zsig37 polypeptides would be useful for such purposes.

The collagen and C1q binding capabilities of zsig37 would be useful to pacify damaged collagenous tissues preventing platelet adhesion, activation or aggregation, and the activation of inflammatory processes which lead to the release of toxic oxygen products. By rendering the exposed tissue inert towards such processes as complement activity, thrombotic activity and immune activation, zsig37 polypeptides, fragments, fusions, antibodies, agonists or antagonists would be useful in reducing the injurious effects of ischemia and reperfusion. In particular, such injuries would include trauma injury ischemia, intestinal strangulation, and injury associated with pre- and post-establishment of blood flow. Zsig37 would be useful in the treatment of cardiopulmonary bypass ischemia and recesitation, myocardial infarction and post trauma vasospasm, such as stroke or percutanious transluminal angioplasty as well as accidental or surgical-induced vascular trauma.

Zsig37 polypeptides, fragments, fusions, antibodies, agonists or antagonists would also be useful to pacify prosthetic biomaterials and surgical equipment to render the surface of the materials inert towards complement activation, thrombotic activity or immune activation. Such materials include, but are not limited to, collagen or collagen fragment-coated biomaterials, gelatin-coated biomaterials, fibrin-coated biomaterials, fibronectin-coated biomaterials, heparin-coated biomaterials, collagen and gel-coated stents, arterial grafts, synthetic heart valves, artificial organs or any prosthetic application exposed to blood that will bind zsig37 at greater than $1\times10^8$. Coating such materials can be done using methods known in the art, see for example, Rubens, U.S. Pat. No. 5,272,074.

Complement and C1q play a role in inflammation. The complement activation is initiated by binding of C1q to immunoglobulins (Johnston, *Pediatr. Infect. Dis. J.* 12:933–41, 1993; Ward and Ghetie, *Therap. Immunol.* 2:77–94, 1995). Inhibitors of C1q and complement would be useful as anti-inflammatory agents. Such application can be made to prevent infection. Additionally, such inhibitors can be administrated to an individual suffering from inflammation mediated by complement activation and binding of immune complexes to C1q. Zsig37 polypeptides, fragments, fusion proteins, antibodies, agonists or antagonists would be useful in methods of mediating wound repair, enhancing progression in wound healing by overcoming impaired wound healing. Progression in wound healing would include, for example, such elements as a reduction in inflammation, fibroblasts recruitment, wound retraction and reduction in infection.

Ability of tumor cells to bind to collagen may contribute to the metastasis of tumors. Inhibitors of collagen binding are also useful for mediating the adhesive interactions and metastatic spread of tumors (Noeske-Jungbult et al., U.S. Pat. No. 5,723,312).

Zsig37 was found to induce vasodilatation in norepinepherin-contracted aortic rings using the procedures of Dainty et al., *J. Pharmacol.* 100:767, 1990 and Rhee et al., *Neurotox.* 16:179, 1995, as is described below in greater detail.

Platelet adhesion, activation and aggregation can be evaluated using methods described herein or known in the art, such as the platelet aggregation assay (Chiang et al., *Thrombosis Res.* 37:605–12, 1985) and platelet adhesion assays (Peerschke and Ghebrehiwet, *J. Immunol.* 144:221–25, 1990) Inhibition of C1q and the complement pathway can be determined using methods disclosed herein or know in the art, such as described in Suba and Csako, *J. Immunol.* 117:304–9, 1976. Assays for platelet adhesion to collagen and inhibition of collagen-induced platelet aggregation can be measured using methods described in Keller et al., *J. Biol. Chem.* 268:5450–6, 1993; Waxman and Connolly, *J. Biol. Chem.* 268:5445–9, 1993; Noeske-Jungblut et al., *J. Biol. Chem.* 269:5050–3 or 1994 Deckmyn et al., *Blood* 85:712–9, 1995.

Various in vitro and in vivo models are available for assessing the effects of zsig37 polypeptides, fragments, fusion proteins, antibodies, agonists and antagonists on ischemia and reperfusion injury. See for example, Shandelya et al., *Circulation* 88:2812–26, 1993; Weisman et al., *Science* 249:146–151, 1991; Buerke et al., *Circulation* 91:393–402, 1995; Horstick et al., *Circulation* 95:701–8, 1997 and Burke et al., *J. Phar. Exp. Therp.* 286:429–38, 1998. An ex vivo hamster platelet aggregation assay is described by Deckmyn et al., ibid. Bleeding times in hamsters and baboons can be measured following injection of zsig37 polypeptides using the model described by Deckmyn et al., ibid. The formation of thrombus in response to administration of proteins of the present invention can be measured using the hamster femoral vein-thrombosis model is provided by Deckmyn et al., ibid. Changes in platelet adhesion under flow conditions following administration of zsig37 can be measured using the method described in Harsfalvi et al., *Blood* 85:705–11, 1995.

Complement inhibition and wound healing can be Zsig37 polypeptides, fragments, fusion proteins, antibodies, agonists or antagonists be assayed alone or in combination with other know inhibitors of collagen-induced platelet activation and aggregation, such as palldipin, moubatin or calin, for example.

Zsig37 polypeptides, fragments, fusion proteins, antibodies, agonists or antagonists can be evaluated using methods described herein or known in the art, such as healing of dermal layers in pigs (Lynch et al., *Proc. Natl. Acad. Sci. USA* 84: 7696–700, 1987) and full-thickness skin wounds in genetically diabetic mice (Greenhalgh et al., *Am. J. Pathol.* 136: 1235–46, 1990), for example. The polypeptides of the present invention can be assayed alone or in combination with other known complement inhibitors as described above.

In addition, zsig37 polypeptides, fragments, fusions agonists or antagonists thereof may be therapeutically useful for anti-microbial applications. For example, complement component C1q plays a role in host defense against infectious agents, such as bacteria and viruses. C1q is known to exhibit several specialized functions. For example, C1q triggers the complement cascade via interaction with bound antibody or C-reactive protein (CRP). Also, C1q interacts directly with certain bacteria, RNA viruses, mycoplasma, uric acid crystals, the lipid A component of bacterial endotoxin and membranes of certain intracellular organelles. C1q binding to the C1q receptor is believed to promote phagocytosis. C1q also appears to enhance the antibody formation aspect of the host defense system. See, for example, Johnston, *Pediatr. Infect. Dis. J.* 12(11): 933–41, 1993. Thus, soluble C1q-like molecules may be useful as anti-microbial agents, promoting lysis or phagocytosis of infectious agents.

The positively charged, extracellular, triple helix, collagenous domains of C1q and macrophage scavenger receptor were determined to play a role in ligand binding and were shown to have a broad binding specificity for polyanions (Acton et al., *J. Biol. Chem.* 268:3530–37, 1993). Lysophospholipid growth factor (lysophosphatidic acid, LPA) and other mitogenic anions localize at the site of damaged tissues and assist in wound repair. LPA exerts many biological effects including activation of platelets and up-regulation of matrix assembly. It is thought that LPA synergizes with other blood coagulation factors and mediates wound healing.

The collagenous domains of proteins such as C1q and macrophage scavenger receptor are know to bind acidic phospholipids such as LPA. A 9 mer region of the collagen domain of zsig37, amino acid residues 127–135 of SEQ ID NO:2, shares sequence homology with the collagen domain found on C1q and macrophage scavenger receptor. The interaction of zsig37 polypeptides, fragments, fusions, agonists or antagonists with mitogenic anions such as LPA can be determined using assays known in the art, see for example, Acton et al., ibid. Inhibition of inflammatory processes by polypeptides and antibodies of the present invention would also be useful in preventing infection at the wound site.

For pharmaceutical use, the proteins of the present invention can be formulated with pharmaceutically acceptable carriers for parenteral, oral, nasal, rectal, topical, transdermal administration or the like, according to conventional methods. Preferably administration is made at or near the site of vascular injury. In general, pharmaceutical formulations will include a zsig37 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton Pa., 19$^{th}$ ed., 1995. Therapeutic doses will generally be determined by the clinician according to accepted standards, taking into account the nature and severity of the condition to be treated, patient traits, etc. Determination of dose is within the level of ordinary skill in the art.

As used herein a "pharmaceutically effective amount" of a zsig37 polypeptide, fragment, fusion protein, agonist or antagonist is an amount sufficient to induce a desired biological result. The result can be alleviation of the signs, symptoms, or causes of a disease, or any other desired alteration of a biological system. For example, an effective amount of a zsig37 polypeptide is that which provides either subjective relief of symptoms or an objectively identifiable improvement as noted by the clinician or other qualified observer. Such an effective amount of a zsig37 polypeptide would provide, for example, inhibition of collagen-activated platelet activation and the complement pathway, including C1q, increase localized blood flow within the vasculature of a patient and/or reduction in injurious effects of ischemia and reperfusion. Effective amounts of the zsig37 polypeptides can vary widely depending on the disease or symptom to be treated. The amount of the polypeptide to be administered and its concentration in the formulations, depends upon the vehicle selected, route of administration, the potency of the particular polypeptide, the clinical condition of the patient, the side effects and the stability of the compound in the formulation. Thus, the clinician will employ the appropriate preparation containing the appropriate concentration in the formulation, as well as the amount of formulation administered, depending upon clinical experience with the patient in question or with similar patients. Such amounts will depend, in part, on the particular condition to be treated, age, weight, and general health of the patient, and other factors evident to those skilled in the art. Typically a dose will be in the range of 0.01–100 mg/kg of subject. In applications such as balloon catheters the typical dose range would be 0.05–5 mg/kg of subject. Doses for specific compounds may be determined from in vitro or ex vivo studies in combination with studies on experimental animals. Concentrations of compounds found to be effective in vitro or ex vivo provide guidance for animal studies, wherein doses are calculated to provide similar concentrations at the site of action.

The invention is further illustrated by the following non-limiting examples.

EXAMPLE 1

Extension of EST Sequence

The novel zsig37 polypeptide-encoding polynucleotides of the present invention were initially identified by selecting an EST from an EST database, predicting a protein sequence based thereupon, and searching known sequence databases for the secreted protein that is most homologous to predicted protein based on the EST. ESTs that potentially encode proteins having biologically interesting homology to known secreted proteins were identified for further study. A single EST sequence was discovered and predicted to be homologous to adipocyte specific protein. See, for example, Scherer et al., *J. Biol. Chem.* 270(45): 26746–9, 1995. To identify the corresponding cDNA, a clone considered likely to contain the entire coding sequence was used for sequencing. Using an Invitrogen S.N.A.p.™ Miniprep kit (Invitrogen, Corp., San Diego, Calif.) according to manufacturer's instructions a 5 ml overnight culture in LB+50 μg/ml ampicillin was prepared. The template was sequenced on an ABIPRISM™ model 377 DNA sequencer (Perkin-Elmer Cetus, Norwalk, Conn.) using the ABI PRISM™ Dye Terminator Cycle Sequencing Ready Reaction Kit (Perkin-Elmer Corp.) according to manufacturer's instructions. Oligonucleotides ZC695 (SEQ ID NO: 5), ZC694 (SEQ ID NO: 6) to the SP6 and T7 promoters on the clone-containing vector were used as sequencing primers. Oligonucleotides ZC13210 (SEQ ID NO: 7), ZC13588 (SEQ ID NO: 8), ZC13532 (SEQ ID NO: 9), ZC13641 (SEQ ID NO: 10), ZC13586 (SEQ ID NO: 11), ZC13651 (SEQ ID NO: 12), ZC13622 (SEQ ID NO: 13), ZC13625 (SEQ ID NO: 14), ZC13650 (SEQ ID NO: 15), ZC13589 (SEQ ID NO: 16), ZC13624 (SEQ ID NO: 17), ZC13531 (SEQ ID NO: 18), ZC13587 (SEQ ID NO: 19), and ZC13623 (SEQ ID NO: 20) were used to complete the sequence from the clone. Sequencing reactions were carried out in a Hybaid OmniGene Temperature Cycling System (National Labnet Co., Woodbridge, N.Y.). SEQUENCHER™ 3.0 sequence analysis software (Gene Codes Corporation, Ann Arbor, Mich.) was used for data analysis. The resulting 2769 bp sequence is disclosed in SEQ ID NO: 1. Comparison of the originally derived EST sequence with the sequence represented in SEQ ID NO: 1 showed that there was one base pair ambiguity (an unknown "N" residue) and no base pair insertions which resulted in the identification of leucine in resolution of the ambiguity and zero frame shifts between the deduced amino acid sequences.

EXAMPLE 2

Tissue Distribution

Northerns were performed using Human Multiple Tissue Blots from Clontech (Palo Alto, Calif.). A 30 base DNA probe (ZC12447; SEQ ID NO: 4) to the 5' end of the nucleotide sequence of the mature protein shown in SEQ ID NO: 1 was radioactively labeled with $^{32}$P using T4 polynucleotide kinase and forward reaction buffer (GIBCO BRL, Gaithersburg, Md.) according to the manufacturer's specifications. The probe was purified using a NUCTRAP push column (Stratagene Cloning Systems, La Jolla, Calif.). EXPRESSHYB (Clontech, Palo Alto, Calif.) solution was used for prehybridization and as a hybridizing solution for the Northern blots. Hybridization took place overnight at 50° C., and the blots were then washed in 2×SSC and 0.1% SDS at RT, followed by a wash in 1×SSC and 0.1% SDS at 68° C. (about 5° C. less than the melting point). One transcript size was observed at approximately 2.8 kb. Signal intensity was highest for heart and placenta, with relatively less intense signals in kidney, ovary, adrenal gland and skeletal muscle and lower signals in a wide variety of other tissues present on the Northern blot.

Additional Northern Blot Analysis was done using a Gut Northern Tissue Blot. The blot was prepared using mRNA from human colorectal adenocarcinoma cell line SW480 (Clontech, Palo Alto, Calif.), human small intestine tissue (Clontech), human stomach tissue (Clontech), human intestinal smooth muscle cell line (Hism; ATCC No. CRL-1692; American Type Culture Collection, 12301 Parklawn Drive, Rockville, Md.), normal human colon cell line (FHC; ATCC No. CRL-1831; American Type Culture Collection) and human normal fetal small intestine cell line (FHs74 Int.; ATCC No. CCL241; American Type Culture Collection).

Total RNAs were isolated from Hism, FHC and FHs74 Int. by acid guanidium method (Cheomczynski et al., *Anal. Biochem.* 162:156–9, 1987). The polyA$^+$ RNAs were selected by eluting total RNA through a column that retains polyA$^+$ RNAs (Aviv et al., *Proc. Nat. Acad. Sci.* 69:1408–12, 1972). 2 µg of polyA$^+$ RNA from each sample was separated out in a 1.5% agarose gel in 2.2 M formaldehyde and phosphate buffer. The RNAs were transferred onto Nytran membrane (Schleicher and Schuell, Keene, N.H.) in 20×SSC overnight. The blot was treated in the UV Stratalinker 2400 (Stratagene, La Jolla, Calif.) at 0.12 Joules. The bolt was then baked at 80° C. for one hour.

Full length cDNA (shown in SEQ ID NO: 1) was amplified by PCR and radiolabeled with $^{32}$P dCTP using a Rediprime pellet kit (Amersham, Arlington Heights, Ill.) according to the manufacturer's specifications. The blot was hybridized in EXPRESSHYB (Clontech) at 56° C. overnight. The blot was washed at room temperature in 2×SSC and 0.1% SDS, then in 2×SSC and 0.1% SDS at 65° C., and finally at 65° C. in 0.1×SSC and 0.1% SDS. Results showed that zsig37 hybridized to all tissues except the human intestinal smooth muscle cell line HISM.

EXAMPLE 3

Chromosomal Mapping of the Zsiq37 Gene

The zsig37 gene was mapped to human chromosome 17, region 17q25.2, by PCR using the NIGMS Human/Rodent Somatic Cell Hybrid Mapping Panel Number 2 (National Institute of General Medical Sciences, Coriell Institute of Medical Research). The panel consists of DNA isolated from 24 human/rodent somatic cell hybrids each retaining one specific human chromosome and the parental DNAs. For the mapping of the zsig37 gene, 20 µl reactions were set up in a 96-well microtiter plate (Stratagene, La Jolla, Calif.) and used in a "RoboCycler Gradient 96" thermal cycler (Stratagene). Each of the 27 PCR reactions consisted of 2 µl 10×KlenTaq PCR reaction buffer (Clontech Laboratories, Inc., Palo Alto, Calif.), 1.6 µl dNTPs mix (2.5 mM each, PERKIN-ELMER, Foster City, Calif.), 1 µl sense primer (SEQ ID NO: 21)., 1 µl antisense primer(SEQ ID NO: 22), 2 µl RediLoad (Research Genetics, Inc.), 0.4 µl 50× Advantage KlenTaq Polymerase Mix (Clontech Laboratories, Inc.), 25 ng of DNA from an individual hybrid clone or control and ddH$_2$O for a total volume of 20 µl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 60° C. and 1.5 minute extension at 72° C., followed by a final 1 cycle extension of 7 minutes at 72° C. The reactions were separated by electrophoresis on a 3% NuSieve GTG agarose gel (FMC Bioproducts, Rockland, Me.).

EXAMPLE 4

Creation of Mammalian Expression Vectors zsiq37NEE/pZP9 and zsiq37 CEE/pZP9

Two expression vectors were prepared for the zsig37 polypeptide, zSIG37NEE/pZP9 and zSIG37CEE/pZP9, wherein the constructs were designed to express a zsig37 polypeptide having a C- or N-terminal Glu-Glu tag.

Zsig37NEE/pZP9

A 800 bp PCR generated zsig-37 DNA fragment was created using ZC15040 (SEQ ID NO:24) and ZC15033 (SEQ ID NO:25) as PCR primers and the template described in Example 1 above. The PCR reaction was incubated at 94° C. for 3 minutes, and then run for 5 cycles of 94° C. for 30 seconds, 30° C. for 20 seconds and 72° C. for 1 minute, followed by 25 cycles at 94° C. for 30 seconds, 64° C. for 20 seconds and 72° C. for 1 minute. A 5 minute extension at 72° C. followed. The resultant PCR product was then run on a 0.9% TBE agarose gel with 1× TBE buffer. A band of the predicted size was excised and the DNA was purified from the gel with a Qiaex II® resin (Qiagen) according the manufacturer's instructions. The DNA was digested with the restriction enzymes Bam HI and Xba I, followed by extraction and precipitation.

The excised, restriction digested zsig37 DNA fragment was subcloned into plasmid NEE/pZP9 which had been cut with the restriction enzymes Bam HI and Xba I. The zsig37NEE/pZP9 expression vector incorporates the TPA leader and attaches a Glu-Glu tag (SEQ ID NO:26) to the N-terminal of the zsig37 polypeptide-encoding polynucleotide sequence. Plasmid NEE/pZP9 (deposited at the American Type Culture Collection, 12301 Parklawn Drive, Rockville, Md., ATCC No. 98668) is a mammalian expression vector containing an expression cassette having the mouse metallothionein-1 promoter, a TPA leader peptide followed by the sequence encoding the Glu-Glu tag (SEQ ID NO:26), multiple restriction sites for insertion of coding sequences, and a human growth hormone terminator. The plasmid also contains an *E. coli* origin of replication, a mammalian selectable marker expression unit having an SV40 promoter, enhancer and origin of replication, a DHFR gene and the SV40 terminator.

zsig376CEE/pZP9

A 866 bp PCR generated zsig37 DNA fragment was created in accordance with the procedure set forth above using ZC15721 (SEQ ID NO:27) and ZC15035 (SEQ ID NO:28) as PCR primers. The purified PCR fragment was digested with the restriction enzymes Eco RI and Bam HI, gel purified using a Qiaex II resin as described above.

The excised and restriction digested zsig37 DNA was subcloned into plasmid CEE/pZP9 which had been cut with Eco RI and Bam HI. The zsig37CEE/pZP9 expression vector uses the native zsig37 signal peptide, and the Glu-Glu epitope (SEQ ID NO:26) is attached at the C-terminus as a purification aid. Plasmid CEE/pZP9 (deposited at the American Type Culture Collection, 12301 Parklawn Drive, Rockville, Md., ATCC No. 98668) is a mammalian expression vector containing an expression cassette having the mouse metallothionein-1 promoter, multiple restriction sites for insertion of coding sequences, a sequence encoding the Glu-Glu tag (SEQ ID NO:26), a stop codon and a human growth hormone terminator. The plasmid also has an *E. coli* origin of replication, a mammalian selectable marker expression unit having an SV40 promoter, enhancer and origin of replication, a DHFR gene and the SV40 terminator.

For the N- and C-tagged constructs, about 30 ng of the restriction digested inserts and 50 ng of the corresponding vectors were ligated at room temperature for 4 hours. One microliter of each ligation reaction was independently electroporated into DH10B competent cells (GIBCO BRL, Gaithersburg, Md.) according to manufacturer's direction and plated onto LB plates containing 50 mg/ml ampicillin, and incubated overnight.

Colonies were screened by PCR as described above. For zsig37NEE/pZP9 and zsig37CEE/pZP9 screens the primers were ZC13006 (SEQ ID NO:29) and ZC13007 (SEQ ID NO:20). The PCR reaction was incubated at 94° C. for 2.5 minutes, and then run for 25 cycles of 94° C. for 10 seconds, 58° C. for 20 seconds and 72° C. for 1 minute. A 5 minute extension at 72° C. followed. The insert sequence of positive clones, 1013 bp for zsig37NEE and a 950 bp fragment for zsig37CEE were verified by sequence analysis. A large scale plasmid preparation was done using a QIAGEN® Maxi prep kit (Qiagen) according to manufacturer's instructions.

EXAMPLE 5

Transfection and Expression of zsiq37NEE and CEE Polypeptides

BHK 570 cells (ATCC No. CRL-10314) were plated in 10 cm tissue culture dishes and allowed to grow to approximately 50 to 70% confluency overnight at 37° C., 5% $Co_2$, in DMEM/FBS media (DMEM, Gibco/BRL High Glucose, (Gibco BRL, Gaithersburg, Md.), 5% fetal bovine serum (Hyclone, Logan, Utah), 2 $\mu$M L-glutamine (JRH Biosciences, Lenexa, Kans.), 1 $\mu$M sodium pyruvate (Gibco BRL)). The cells were then transfected with the plasmid zsig37NEE/pZP9 (N-terminal Glu-Glu tag) or zsig37CEE/pZP9 (C-terminal Glu-Glu tag), using Lipofectamine™ (Gibco BRL), in serum free (SF) media formulation (DMEM, Gibco/BRL High Glucose, (Gibco BRL, Gaithersburg, Md.), 2 mM L-glutamine, 2 mM sodium pyruvate, 10 ug/ml transferrin, 5 $\mu$g/ml insulin, 10 $\mu$g/ml fetuin and 2 ng/ml selenium). Sixteen micrograms of zsig37NEE/pZP9 and 16 $\mu$g of zsig37CEE/pZP9 were separately diluted into 15 ml tubes to a total final volume of 640 $\mu$l SF media. In separate tubes, 35 $\mu$l of Lipofectamine™ (Gibco BRL) was mixed with 605 $\mu$l of SF medium. The Lipofectamine™ mix was added to the DNA mix and allowed to incubate approximately 30 minutes at room temperature. Five milliliters of SF media was added to the DNA:Lipofectamine™ mixture. The cells were rinsed once with 5 ml of SF media, aspirated, and the DNA:Lipofectamine™ mixture was added. The cells were incubated at 37° C. for five hours, then 6.4 ml of DMEM/10% FBS, 1% PSN media was added to the plate. The plate was incubated at 37° C. overnight and the DNA:Lipofectamine™ mixture was replaced with fresh FBS/DMEM media the next day. On day 2 post-transfection, the cells were split into the selection media (ESTEP #1 with 1 $\mu$M MTX) in 150 mm plates at 1:50, 1:100 and 1:200. The plates were refed at day 5 post-transfection with fresh selection media.

Screening Colonies

Approximately 10–12 days post-transfection, one 150 mm culture dish of methotrexate resistant colonies was chosen from each transfection, the media aspirated, the plates washed with 10 ml serum-free ESTEP 2 media (668.7 g/50 L DMEM (Gibco), 5.5 g/50 L pyruvic acid, sodium salt 96% (Mallinckrodt), 185.0 g/50 L $NaHCO_3$ (Mallinkrodt), 5.0 mg/ml, 25 ml/50 L insulin, 10.0 mg/ml and 25 ml/50 L transferrin). The wash media was aspirated and replaced with 5 ml serum-free ESTEP 2. Sterile Teflon mesh (Spectrum Medical Industries, Los Angeles, Calif.) pre-soaked in serum-free ESTEP 2 was then placed over the cells. A sterile nitrocellulose filter pre-soaked in serum-free ESTEP 2 was then placed over the mesh. Orientation marks on the nitrocellulose were transferred to the culture dish. The plates were then incubated for 5–6 hours in a 37° C., 5% $CO_2$ incubator. Following incubation, the filter was removed, and the media aspirated and replaced with DMEM/5% FBS, 1×PSN (Gibco BRL) media. The filter was then placed into a sealable bag containing 50 ml buffer (25 mM Tris, 25 mM glycine, 5 mM β-mercaptoethanol) and incubated in a 65° C. water bath for 10 minutes. The filters were blocked in 10% nonfat dry milk/Western A buffer (Western A: 50 mM Tris pH 7.4, 5 mM EDTA, 0.05% NP-40, 150 mM NaCl and 0.25% gelatin) for 15 minutes at room temperature on a rotating shaker. The filter was then incubated with an anti-Glu-Glu antibody-HRP conjugate at a 1:1000 dilution in 2.5% nonfat dry milk/Western A buffer (Western A: 50 mM Tris pH 7.4, 5 mM EDTA, 0.05% NP-40, 150 mM NaCl and 0.25% gelatin) overnight at 4° C. on a rotating shaker. The filter was then washed three times at room temperature in PBS plus 0.1% Tween 20, 5–15 minutes per wash. The filter was developed with ECL reagent (Amersham Corp., Arlington Heights, Ill.) according the manufacturer's directions and exposed to film (Hyperfilm ECL, Amersham) for approximately 5 minutes.

The film was aligned with the plate containing the colonies. Using the film as a guide, suitable colonies were selected. Sterile, 3 mm coloning discs (PGC Scientific Corp., Frederick, Md.) were soaked in trypsin, and placed on the colonies. Twelve colonies for each construct were transferred into 200 $\mu$l of selection medium in a 96 well plate. A series of seven, two-fold dilutions were carried out for each colony. The cells were grown for one week at 37° C. at which time the wells which received the lowest dilution of cells which are now at the optimum density were selected, trypsinized and transferred to a 12 well plate containing selection media. The 150 mm culture dish was also trypsinized and the remainder of the cells were pooled and subjected to western analysis and mycoplasma testing. The pool was frozen for storage.

The clones were expanded directly from the 12 well plate into two T-75 flasks. One flask was kept to continue cell growth, the second flask was grown in serum-free ESTEP 2 which was harvested for Western Blot. analysis. Clones of each of the expression constructs, based on Western blot analysis, were selected, pooled and transferred to large scale culture.

EXAMPLE 6

Large Scale Mammalian Expression of zsiq37CEE

One T-162 flask, containing confluent cells expressing zsig37CEE and one containing zsig37NEE obtained from the expression procedure described above, were expanded into four T-162 flasks each. One of the four resulting flasks was used to freeze down four cryovials, and the other three flasks were used to generate a Nunc cell factory.

The cells from the three T-162 flasks of zsig37CEE and zsig37NEE were used to independently seed two Nunc cell factories (10 layers, commercially available from VWR). Briefly, the cells from the T-162 flasks described above were detached using trypsin, pooled, and added to 1.5 liters ESTEP1 media (668.7 g/50 L DMEM (Gibco), 5.5 g/50 L pyruvic acid, sodium salt 96% (Mallinckrodt), 185.0 g/50 L $NaHCO_3$ (Mallinkrodt), 5.0 mg/ml and 25 ml/50 L insulin (JRH Biosciences), 10.0 mg/ml and 25 ml/50 L transferrin (JRH Biosciences), 2.5 L/50 L fetal bovine serum (characterized) (Hyclone), 1 $\mu$M MTX, with pH adjusted to 7.05+/−0.05) prewarmed to 37° C. The media containing the cells was then poured into the Nunc cell factories via a funnel. The cell factories were placed in a 37° C./5.0% $CO_2$ incubator.

At 80–100% confluence, a visual contamination test (phenol red color change) was performed on the contents of the Nunc cell factories. Since no contamination was observed, supernatant from the confluent factories was poured into a small harvest container, sampled and discarded. The adherent cells were then washed once with 400 ml PBS. To detach the cells from the factories, 100 mls of trypsin was added to each and removed and the cells were then incubated for 5 to 10 minutes in the residual trypsin. The cells were collected following two, 200 ml washes with ESTEP1 media. To each of ten ESTEP1 media-containing bottles (1.5 liters each, at 37° C.) was added 40 mls of collected cells. One 1.5 liter-bottle was then used to fill one Nunc factory. Each cell factory was placed in a 37° C./5.0% $CO_2$ incubator.

At 80–90% confluence, a visual contamination test (phenol red color change) was performed on the Nunc cell factories. Since no contamination was observed, supernatant from the confluent factories was poured into a small harvest container, sampled and discarded. Cells were then washed once with 400 ml PBS. 1.5 liters of ESTEP2 media (668.7 g/50 L DMEM (Gibco), 5.5 g/50 L pyruvic acid, sodium salt 96% (Mallinckrodt), 185.0 g/50 L $NaHCO_3$ (Mallinkrodt), 5.0 mg/ml, 25 ml/50 L insulin, 10.0 mg/ml and 25 ml/50 L transferrin) was added to each Nunc cell factory. The cell factories were incubated at 37° C./5.0% $CO_2$.

At approximately 48 hours a visual contamination test (phenol red color change) was performed on the Nunc cell factories. Supernatant from each factory was poured into small harvest containers. Fresh serum-free media (1.5 liters) was poured into each Nunc cell factory, and the factories were incubated at 37° C./5.0% $CO_2$. One ml of supernatant harvest for each construct was transferred to a microscope slide, and subjected to microscopic analysis for contamination. The contents of the small harvest containers for each construct were pooled and immediately filtered. A second harvest was then performed, substantially as described above at 48 hours and the cell factories were discarded thereafter. An aseptically assembled filter train apparatus was used for aseptic filtration of the harvest supernatant (conditioned media). Assembly was as follows: tubing was wire-tied to an Opti-Cap filter (Millipore Corp., Bedford, Mass.) and a Gelman Supercap 50 filter (Gelman Sciences, Ann Arbor, Mich.). The Supercap 50 filter was also attached to a sterile capped container located in a hood; tubing located upstream of the Millipore Opti-cap filter was inserted into a peristaltic pump; and the free end of the tubing was placed in the large harvest container. The peristaltic pump was run between 200 and 300 rpm, until all of the conditioned media passed through the 0.22 $\mu$m final filter into a sterile collection container. The filtrate was placed in a 4° C. cold room pending purification. The media was concentrated 10× with a Millipore 5 kDA cut off concentrator (Millipore Corp., Bedford, Mass.) according to manufacturer's direction and subjected to Western Blot analysis using an anti-FLAG tag antibody (Kodak).

Zsig37CEE:

5 T-162 Flasks=0.12 mg/L, 38 kDa;

1 Factory, FBS=0.12 mg/L, 38 kDa;

10 Factories, FBS=0.12 mg/L, 38 kDa;

10 Factories (#1), SF=1.2 mg/L, 38 kDa; and

10 Factories (#2), SF=3.56 mg/L, 38 kDa

Zsiq37NEE:

5 T-162 Flasks=0.137 mg/L, 35 kDa;

1 Factory, FBS=0.137 mg/L, 35 kDa;

10 Factories, FBS=0.137 mg/L, 35 kDa;

10 Factories (#1), SF=1.37 mg/L, 35 kDa; and

10 Factories (#2), SF=4.11 mg/L, 35 kDa.

EXAMPLE 7

Purification of zsiq37 NEE and zsiq37 CEE

Unless otherwise noted, all operations were carried out at 4° C. The following procedure was used for purifying zsig37 containing N-terminal or C-terminal Glu-Glu (EE) tags. A total of 25 liters of conditioned media from baby hamster kidney (BHK) cells was sequentially sterile filtered through a 4 inch, 0.2 mM Millipore (Bedford, Mass.) OptiCap capsule filter and a 0.2 mM Gelman (Ann Arbor, Mich.) Supercap 50. The material was then concentrated to about 1.3 liters using a Millipore ProFlux A30 tangential flow concentrator fitted with a 3000 kDa cutoff Amicon (Bedford, Mass.) S10Y3 membrane. The concentrated material was again sterile-filtered with the Gelman filter as described above. A mixture of protease inhibitors was added to the concentrated conditioned media to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). A 25.0 ml sample of anti-EE Sepharose, prepared as described below, was added to the sample for batch adsorption and the mixture was gently agitated on a Wheaton (Millville, N.J.) roller culture apparatus for 18.0 h at 4° C.

The mixture was then poured into a 5.0×20.0 cm Econo-Column (Bio-Rad, Laboratories, Hercules, Calif.) and the gel was washed with 30 column volumes of phosphate buffered saline (PBS). The unretained flow-through fraction was discarded. Once the absorbance of the effluent at 280 nM was less than 0.05, flow through the column was reduced to zero and the anti-EE Sepharose gel was washed batch-wise with 2.0 column volumes of PBS containing 0.4 mg/ml of EE peptide (AnaSpec, San Jose, Calif.). The peptide used has the sequence Glu-Tyr-Met-Pro-Val-Asp, SEQ ID NO:31). After 1.0 h at 4° C., flow was resumed and the eluted protein was collected. This fraction was referred to as the peptide elution. The anti-EE Sepharose gel was then washed with 2.0 column volumes of 0.1 M glycine, pH 2.5, and the glycine wash was collected separately. The pH of the glycine-eluted fraction was adjusted to 7.0 by the addition of a small volume of 10×PBS and stored at 4° C. for future analysis if needed.

The peptide elution was concentrated to 5.0 ml using a 15,000 molecular weight cutoff membrane concentrator. (Millipore, Bedford, Mass.) according to the manufacturer's instructions. The concentrated peptide elution was separated from free peptide by chromatography on a 1.5×50 cm Sephadex G-50 (Pharmacia, Piscataway, N.J.) column equilibrated in PBS at a flow rate of 1.0 ml/min using a BioCad Sprint HPLC (PerSeptive BioSystems, Framingham, Mass.). Two-ml fractions were collected and the absorbance at 280 nM was monitored. The first peak of material absorbing at 280 nM and eluting near the void volume of the column was collected. This fraction was pure zsig37 NEE or zsig37 CEE. The pure material was concentrated as described above, analyzed by SDS-PAGE and Western blotting with anti-EE antibodies, and samples were taken for amino acid analysis and N-terminal sequencing. The remainder of the sample was aliquoted, and stored at −80° C. according to our standard procedures.

Electrophoresis of zsig37 NEE on SDS-PAGE gels in the absence of reducing agents, showed one major Coomassie Blue-stained band of apparent molecular weight 39,000 and several minor components of molecular weights between 60,000 and 116,000. All of the bands showed cross reactivity with anti-EE antibodies on Western blots. In the presence of reducing agent, the only band observed was the 39,000 kDa protein, and its Coomassie Blue staining intensity was increased. This band also showed cross-reactivity with the anti-EE antibody on Western blots.

For zsig37 CEE, electrophoresis on SDS-PAGE gels in the absence of reducing agents showed one major Coomassie Blue-stained band of apparent molecular weight 39,000 and several minor components of molecular weights between 60,000 and 116,000. On Western blots, only bands of apparent molecular weights 150,000, 116,000, and 60,000 showed cross-reactivity with the anti-EE antibody. In the presence of reducing agents, only the Coomassie Bluestained band at 39,000 kDa was observed and this material showed cross-reactivity with the anti-EE antibody on Western blots. Under these conditions, a small amount of cross-reactive material was also seen at 150,000 kDa.

Preparation of anti-EE Sepharose

A 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.). and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.), dissolved in TEA, was added to a final concentration of 36 mg/ml of gel. The gel was rocked at room temperature for 45 min and the liquid was removed using the filter unit as described above. Nonspecific sites on the gel were then blocked by incubating for 10 min at room temperature with 5 volumes of 20 mM ethanolamine in 200 mM TEA. The gel was washed with 5 volumes of PBS containing 0.02% sodium azide and stored in this solution at 4° C.

EXAMPLE 8

Adhesion and Proliferation Assays

The ability of zsig37 to stimulate adhesion and spreading of TF-1 cells was assayed as follows. A series of dilutions were prepared from C-terminal Glu-Glu-tagged zsig37, from 10 to 0.0625 µg/ml, in either PBS or ELISA coating buffer (0.1 M $NaCO_3$) and each was plated into a 96 well plate (Costar, Pleasanton, Calif.) at 100 µl/well. The plates were incubated at 37° C., 5% $CO_2$ for 2 hours. The plates were then washed 3× with RPMI/10% FBS (RPMI 1640, 2 mM L-glutamine, 110 µg/ml sodium pyruvate, PSN and 10% heat inactivated fetal bovine serum) and allowed to block for 15 minutes.

TF-1 cells (derived from acute myeloid leukemia cells) were resuspended in RPMI/10% FBS and plated into at 10,000 cells/well into the zsig37CEE-coated 96 well plates at a final volume of 120 µl/well. The plate was incubated at 37° C. under 5% $CO_2$ for 2 hours. The plates were then washed 3× with PBS and 200 µl/well growth media (RPMI/ 10% FBS, 5 ng/ml GM-CSF) was added. The cells were microscopically inspected before and after the wash.

A dye incorporation assay was also used to quantitatively measure the number of adherent cells based on a colorimetric change and an increase in fluorescent signal. Alamar Blue™ (AccuMed, Chicago, Ill.) was added to the 96 well plates and the cells were incubated at 37° C. under 5% $CO_2$ overnight. The plates were then scanned using a fluorometer with excitation wavelength of 544 nm and emission wavelength of 590 nm. There were more adherent cells on the zsig37CEE-PBS coated plates than on the zsig37CEE-0.1 M $NaCO_3$ coated plates. Addition of soluble zsig37 did not block adhesion of cells to the bound zsig37.

A second assay was done using TF-1, DA-1 (an IL-3 dependent cell line derived from the lymph node of a mouse with a B-cell lymphoma by outgrowth in IL-3 media (provided by Dr. Kenneth Kaushansky, University of Washington, Seattle, Wash.)), pre-B (p53−/− mouse marrow cells, IL-7 dependent, B220+, Thyl low, Sca-1+), and A7BaF-3 cell lines as described above at 5,000 cells/well. BHK cells were also plated at 500 cells/well. Zsig37 enhanced the growth of A7-BaF-3 cells and slightly inhibited growth of DA-1 cells.

EXAMPLE 9

Mouse Ortholog Sequence

The novel human zsig37 polypeptide-encoding polynucleotides of the present invention were used to screen a mouse EST database for homologous mouse sequences. A single EST sequence was discovered and predicted to the human zsig37 sequence. To identify the corresponding cDNA, a clone considered likely to contain the entire coding sequence was used for sequencing. Using an Invitrogen S.N.A.P.™ Miniprep kit (Invitrogen Corp.) according to manufacturer's instructions a 5 ml overnight culture in LB+50 µg/ml ampicillin was prepared. The template was sequenced on an ABIPRISM™ model 377 DNA sequencer (Perkin-Elmer Cetus, Norwalk, Conn.) using the ABI PRISM™ Big Dye Terminator Cycle Sequencing Ready Reaction Kit (Perkin-Elmer Corp.) according to manufacturer's instructions. Oligonucleotides ZC694 (SEQ ID NO:6), ZC6768 (SEQ ID NO:32), ZC18297 (SEQ ID NO:33), ZC18298 (SEQ ID NO:34), ZC18402 (SEQ ID NO:35), ZC18403 (SEQ ID NO:36), ZC18456 (SEQ ID NO:37), ZC18457 (SEQ ID NO:38), ZC18560 (SEQ ID NO:39), ZC18561 (SEQ ID NO:40), ZC18687 (SEQ ID NO:41) and ZC18688 (SEQ ID NO:42) were used to complete the sequence from the clone. Sequencing reactions were carried out in a Hybaid OmniGene Temperature Cycling System (National Labnet Co., Woodbridge, N.Y.).

SEQUENCHER™ 3.1 sequence analysis software (Gene Codes Corporation, Ann Arbor, Mich.) was used for data analysis. The resulting 2559 bp sequence is disclosed in SEQ ID NO:43 and the deduced amino acid sequence in SEQ ID NO:44. Alignment with the human zsig37 nucleotide sequence (SEQ ID NO:1) shows 77% identity at the nucleotide level. The putative amino acid sequence (SEQ ID NO:44) has 77% identity with the human polypeptide sequence (SEQ ID NO:2).

EXAMPLE 10

Cell Based Assays

Zsig37 polypeptides were assayed in a high throughput, in vitro assay to identify substances that selectively activate cellular responses in immortalized osteoblast cell lines. A mature osteoblast cell line derived from p53−/− (deficient) mice, CCC4, that is transfected with a plasmid containing an inducible serum response element (SRE) driving the expression of luciferase was used in the assay. These cells also express endogenous PTH, PDGF and bFGF receptors. The stimulation of the SRE and thus the expression of iluciferase in the CCC4 cells indicates that the chemical entity is likely to stimulate mitogenesis in osteoblasts.

CCC4 lines were trypsinized and adjusted to $5 \times 10^4$ cells/ml in plating medium (alpha-MEM, 1% heat inactivated fetal bovine serum, 1 mM Na pyruvate and 2 mM L-glutamate) and plated (200 ul/well) into Dynatech Microlite opaque white microtiter plates (Dynatech, Chantilly, Va.) and incubated overnight at 37° C. 5% $CO_2$. The growth medium was then aspirated and replaced with 50 ul/well assay medium (F-12 HAM, 0.5% bovine serum albumin, 20 mM HEPES, 1 mM Na pyruvate and 2 mM L-glutamate). Serial dilutions of zsig37 were made in assay medium (0.29–1000 ng/ml final assay concentration) and added to the wells. Zsig37 samples were assayed in triplicate. Serum (negative) and bFGF (positive) controls were also used. Final concentration of bFGF was 3 ng/ml. Controls were assayed in quadruplicates. The plates were incubated for 4 hours at 37° C., 5% $CO_2$. The assay medium was then aspirated and the plates were rinsed once with PBS. To each well was then added 25 μl of lysis buffer (Luciferase Assay Reagent, E1501, Promega Corp., Madison, Wis.). The plates were incubated for 15 minutes at room temperature. Fifty microliters/well of luciferase substrate (Luciferase Assay Reagent, E1501, Promega Corp.) was added and the Luciferase activity was detected using a Labsystems LUMINOSKAN® at 2 second/well following a 1 second delay. The average basal (uninduced) signal was subtracted from all readings which are expressed in Table 5 as a percentage of the maximal induction produced by 3 ng/ml bFGF.

Zsig37 stimulates the expression of luciferase in this assay indicating that they stimulate osteoblasts. Zsig37 stimulates at 73 to 75% maximal at 1000 ng/ml.

A counter part growth factor mimetic assay was performed to determine if zsig37 is acting as a growth factor mimetic, particularly tyrosine kinase receptor ligands PDGF, bFGF and EGF (Insulin-R negative). A clonal cell line derived from Swiss 3T3 mice, Swiss 3T3, that is transfected with a plasmid containing an inducible serum response element (SRE) driving the expression of luciferase was used in the assay. These cells also express endogenous PMA, EGF and bFGF receptors. The stimulation of the SRE and thus the expression of luciferase in the Swiss 3T3 cells indicates that the chemical entity is likely mimics the PDGF, bFGF and EGF growth factor activity.

Swiss 3T3 cells were trypsinized and adjusted to $5 \times 10^4$ cells/ml in plating medium, plated and incubated as described above. The growth medium was then aspirated and replaced with 50 ul/well assay medium (F-12 HAM, 0.5% bovine serum albumin, 20 mM HEPES). Serial dilutions of zsig37 were made in assay medium (0.29–1000 ng/ml final assay concentration) and added to the wells. Zsig37 samples were assayed in triplicate. A serum (negative) and bFGF (positive) control to promote cell proliferation were also used. Final concentration of bFGF was 3 ng/ml. Controls were assayed in quadruplicates. The plates were incubated for 5 hours at 37° C., 5% $CO_2$. The assay medium was then aspirated and the plates were rinsed once with PBS. To each well was then added 25 μl of lysis buffer (Luciferase Assay Reagent, E1501, Promega Corp., Madison, Wis.). The plates were incubated for 15 minutes at room temperature. Forty microliters/well of luciferase substrate (Luciferase Assay Reagent, E1501, Promega Corp.) was added and the Luciferase activity was detected using a Labsystems LUMINOSKAN® at 2 second/well following a 1 second delay. The average basal (uninduced) signal was subtracted from all readings which are expressed as a percentage of the maximal induction produced by 3 ng/ml bFGF. A five hour treatment of this cell line with bFGF, BDGF, EGF or PMA leads to a 25–50 fold induction of SRE-luciferase expression.

Zsig37 does not appear to stimulate the expression of luciferase in this assay. Zsig37 stimulates at 0.2 to 0.1% maximal at 1000 ng/ml.

EXAMPLE 10

In vivo Administration of zsiq37 Via Adenoviral Delivery

Twenty four male and 24 female C57B16/J mice, approximately 12 weeks old (Jackson Labs, Bar Harbor, Me.) were weighed, body temperature was measured and food intake monitored daily for four days prior to injection (days −4 to −1). On day 0, the mice were divided into three groups and received 0.1 ml virus (AdV-empty 1.8×1011 virus particles/0.1 ml or AdV-zsig37-CEE 5×1011 virus particles/0.1 ml) by intravenous tail vein injection, or no injection at all. Injection should result in infection of the host's liver and expression of virally delivered gene should commence within 24 hours and continue for 1 to 4 weeks. Three groups of mice were tested. Group 1, untreated, n=8 each male and female. Group 2, AdV-Empty (empty virus), n=8 each male and female. Group 3, AdV-zsig37 CEE, n=8 each male and female.

The animals' body temperatures, weights and the weight of food ingested was monitored during the three week study. No difference was found between the groups.

On day 21 the female mice were euthanized and sacrificed by cervical dislocation, and on day 22 the males were. The animals were exsanguinated and tissues harvested for necropsy.

The standard serum chemistry panel was done at the time of sacrifice. Liver, kidney and metabolic parameters were all within normal ranges. There was, however a difference between the zsig37 treatment group and the empty virus treated group. The zsig37 animals had a higher average lipemic index than the empty virus controls. The difference was not significant, however further investigation was warranted. Total free fatty acids were assayed on the remaining serum from each animal. A statistically significant difference in serum Free Fatty Acid levels was seen between male mice (p=0.0379) receiving empty virus and those receiving zsig37 encoding virus; the zsig37 mice had higher levels. A difference, though not statistically significant, was also seen in females (p=0.3357). Liver, spleen, kidney, thymus, heart and brain were weighed after removal. No difference was found between the treatment groups. Histopathological analysis of these tissues and bone marrow revealed no difference between the treatment groups.

To confirm the above results a second screen was done as above with the following modifications. Three groups; a) untreated and fasted, b) AdV-null and fasted, c) AdV-zsig37-CEE and fasted, containing 20 C57B16/J, 10 each male and female, were tested. The mice were fasted overnight and 100 μl serum was collected to establish a basal level for the following parameters: fasting glucose, TP, alkaline phosphatase, cholesterol, triglycerides, free fatty acids and insulin. Body weights were taken three times a week. On day O, mice were injected into the lateral tail vein with 0.1 ml of the appropriate virus solution. Blood was collected on day 17 following an overnight fast. After 3 weeks the mice were sacrificed and all blood collected. A portion of the blood was mixed with EDTA to look at CBC's and the remainder will be reassayed and screened as described above. Organs were collected and the carcass saved for histopathology.

EXAMPLE 11

Vasodilatation of Aortic Rings

The effect of zsig37 on vasodilatation of aortic rings was measured according to the procedures of (Dainty et al., *J. Pharmacol.* 100:767, 1990 and Rhee et al., *Neurotox.* 16: 179, 1995). Briefly, aortic rings 4 mm in length were taken from 4 month old Sprague Dawley rats and placed in modified Krebs solution (118.5 mM NaCl, 4.6 mM KCl, 1.2 mM $MgSO_4$. 7 $H_2O$, 1.2 mM $KH_2PO_4$, 2.5 mM $CaCl_2$.2 $H_2O$, 24.8 mM $NaHCO_3$ and 10 mM glucose). The rings were then attached to an isometric force transducer (Radnoti Inc., Monrovia, Calif.) and the data recorded with a Ponemah physiology platform (Gould Instrument systems, Inc., Valley View, Ohio) and placed in a 10 ml tissue bath oxygenated (95% $O_2$, 5% $CO_2$) modified Krebs solution. The tissues were adjusted to 1 gram resting tension and allowed to stabilize for one hour before testing. The rings were tested by 5 μl additions of $1 \times 10^{-7}$ M norepinepherin (Sigma Co., St. Louis, Mo.) to a final concentration of about 1×10-9 M and Carbachol, a muscarinic acetylcholine agonist (Sigma Co.) at $2 \times 1^{-7}$ M final, to test the integrity of the rings. After each test the rings were washed three times with fresh buffer, 5 minutes between washes and allowed to rest one hour. To test for vasodilatation, the rings were contracted to two grams and allowed to stabilize for fifteen minutes. Zsig37 was then added to 1, 2 or 3 of the 4 baths, without flushing, and tension on the rings was recorded and compared to the control rings. The rings were then tested for contraction with norepinepherin as described above. Rings were tested at 323, 162, and 81 ng/ml zsig37 but a dose response could not be determined. In order to evaluate the statistical significance of the data, a contingency test was done on all the zsig37 and control rings using dilation as a determinant. Of 10 of the 12 rings tested with zsig37 vasodialated as did 2 of the 7 controls. The Fisher exact P value is 0.045. It was concluded that zsig37 induces vasodilatation in norepinepherin contracted aortic rings.

EXAMPLE 12

Binding of zsig37 to Matrix Proteins

An ELISA (Enzyme-linked Immunosorbant Assay) was used to measure binding of zsig37 to various matrix proteins and complement C1q. The matrix proteins used were Bovine Collagen Type I (Becton Dickinson, Lincoln Park, N.J.) laminin, vitronectin, fibronectin, human collagen Types II, III, IV, V, VI (Chemicon International, Temecula, Calif.). BSA V (Sigma Co.) was used as a negative control. Just prior to use, the proteins were diluted in 2×PBS (Phosphate Buffered Saline, Sigma Co.) to 100 μg/ml and adjusted to pH 7.2 with 0.1 N NaOH. Each protein sample was quadruplicate plated (100 μl/well) into a 96 well plate. The plate was allowed to dry overnight in a laminar flow hood and washed 3 times with 400 μl of 5 mg/ml BSA in 1×PBS and blotted dry. Zsig37 was FITC labeled according to manufacturer's instruction (Pierce, Rockford, Ill.). Into each well was added 100 μl of 1.8 μg/ml zsig37-FITC in 5% BSA, PBS. The plates were incubated for 1.5 hours at room temperature then washed 3 time with 5% BSA, PBS. To each well was then added 100 μl of 1:400 mouse anti-FITC/Biotin (Sigma Co.). The plate was incubated 1.5 hours at room temperature and washed 3 times with 5% BSA, PBS. The plate was then incubated with 100 μl of 1:1000 streptavidin/HRP (Amersham, Piscataway, N.J.) for 1 hour and washed 3 times with 5% BSA, PBS. The plate was then developed using Supersignal® Ultra (Pierce, Rockford, Ill.) according to manufacturer's instruction. After reacting for 1 minute, surplus liquid was removed from the plate by inverting the plate and patting dry. The plate was exposed to X-ray film (Kodak, Rochester, N.Y.).

The results of this screen indicate that only fibronectin and the collagens I, II, III, V and VI bind significantly to zsig37-FITC. Such binding was not seen with laminin, vitronectin, collagen IV or the BSA control.

EXAMPLE 13

Specificity of Zsig37 Binding to Collagen Type VI

The ELISA assay for binding as described in Example 12 was modified to quantitatively evaluate binding. Zsig37-FITC, in a range of 0.4 to 4 μg/ml, was bound to 10 μg of collagen type VI (Chemicon International) as described in above. The luminescence from the Supersignal® reagent was read on a Wallac 1420 plate reader (Wallac, Gaithersburg Md.) and the intensity used as a quantitative measure of the zsig37-FITC bound to the ELISA plate.

Figure 3B:
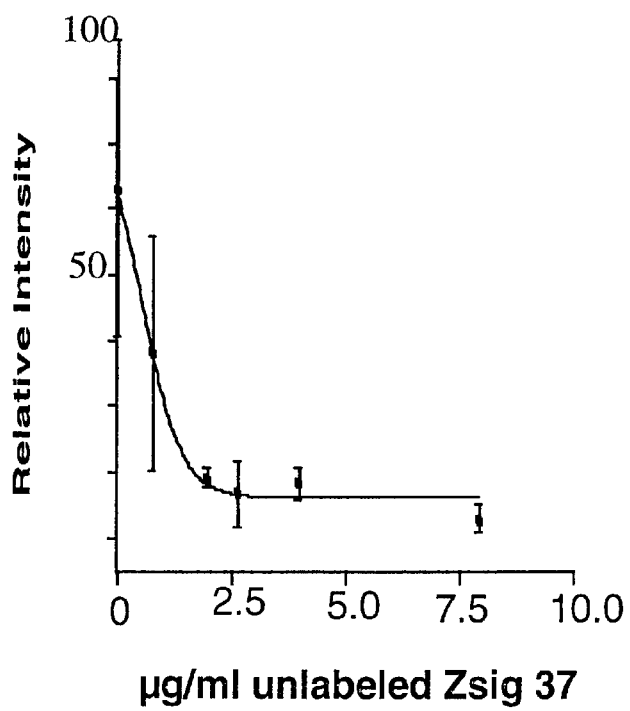
FIG. 3b shows competition of unlabeled zsig37 with FITC labeled zsig37 bound to type VI collagen.

The binding of zsig37 to collagen type VI fits a typical hyperbolic binding curve (FIG. 3a). The bound Zsig37-FITC plated at 0.4 μg/ml can be competed off the collagen by the addition of unlabeled Zsig37 in a range of 0.8 to 8 μg/ml (FIG. 3b). These data would indicate that binding is specific for domains on collagen type VI and is concentration dependent.

EXAMPLE 14

Zsig37 Binding to Complement C1q

Figure 4:
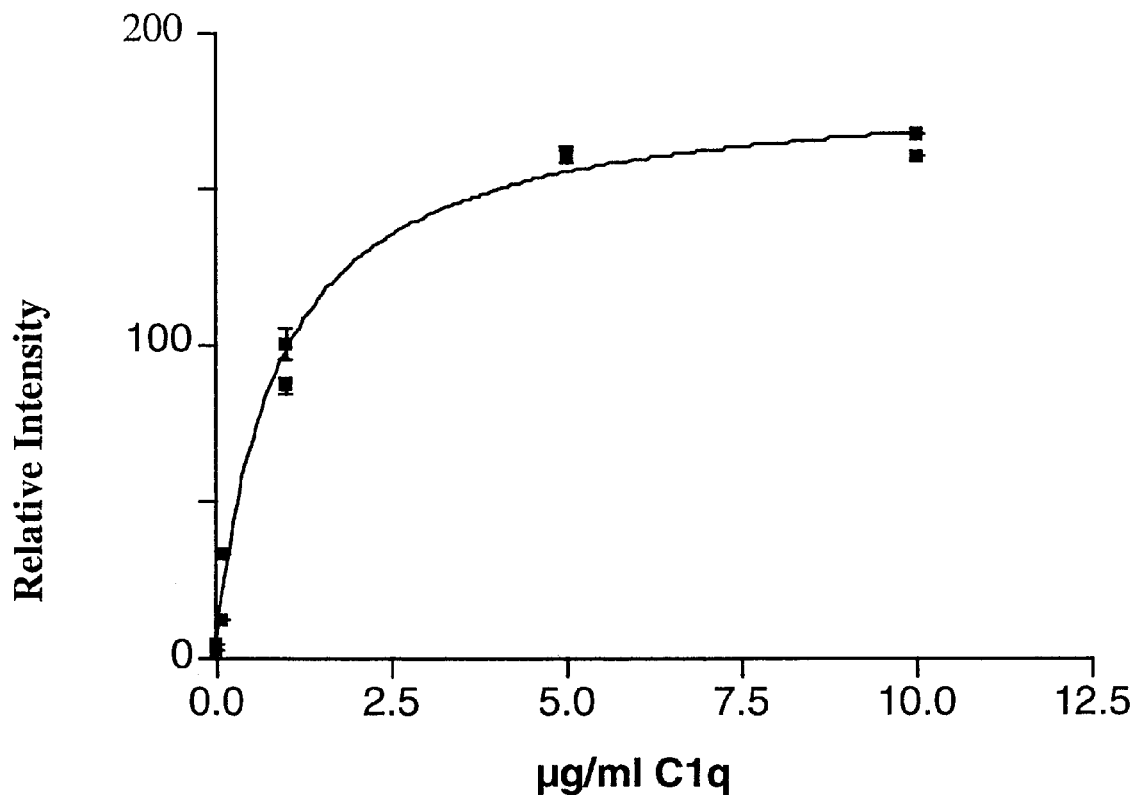
FIG. 4 shows binding of complement C1q-FITC to zsig37.

Zsig37-FITC at 0.2 μg/ml was shown to bind to complement C1q (Sigma Co.) at 0.1 to 10 μg/ml by the method described above in Example 13, (FIG. 4). The amount of binding is concentration dependent and saturable.

EXAMPLE 15

Complement Inhibition by Zsig37

Complement assays were performed in 96 well round bottom plates. Gelatin Veronal buffer containing magnesium and calcium (141 mM NaCl, 1.8 mM sodium barbitol, 3.1 mM Barbituric acid, 0.1% bovine gelatin, 0.5 mM $MgCl_2$ and 0.15 mM $CaCl_2$) was used for all serum and inhibitor dilutions as well as erythrocyte suspensions. Fifty microliters of standardized human Complement serum (Sigma Co.), diluted 1/37.5 (for a final dilution of 1/150) was added to each well. The inhibitor was added in triplicate, 50 μl/well. The serum and inhibitor were incubated for thirty minutes at room temperature. The assay was initiated by the addition of 100 μl of $2 \times 10^8$/ml unsensitized sheep erythrocytes (Colorado Serum Co., Denver, Colo.), sensitized sheep erythrocytes, sensitized using the Hemolysin manufacturer's protocol (BioWhittaker Inc., Walkersville, Md.) and rabbit erythrocytes containing 16 mM EGTA, and 4 mM $Mg^{++}$. A human serum dilution series from 1/50 to 1/400 was also plated as an activity control. Erythrocytes, lysed with distilled water and diluted to 100, 75, 50, 25, and 12.5 percent lysis, were used to quantify Complement percent lysis. The plate was sealed and incubated at 37° C. for 1 hour with mixing every 15 minutes. The reaction was stopped by the addition of 220 mM EDTA, 20 μl/well and the plates centrifuged at 1500× G for 10 minutes. One hundred microliters of supernatant was removed from each well and transferred to a 96 well flat bottom plate for analysis. The plate was read at 415 nM and percent lysis was calculated.

Figure 5:
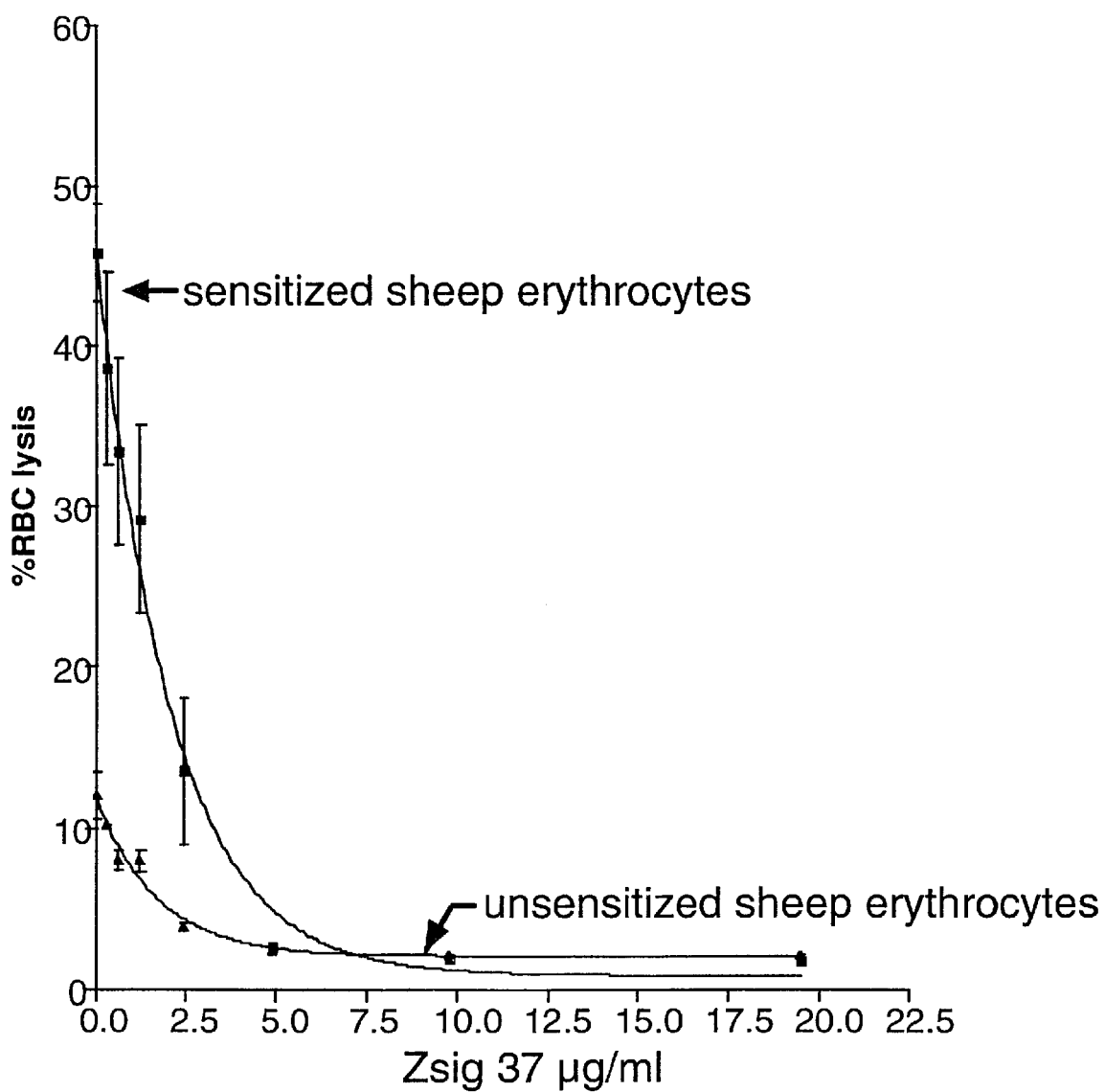
FIG. 5 shows inhibition of human complement activity by zsig37.

Zsig37 was effective in inhibiting the classical pathway with both sensitized and unsensitized sheep erythrocytes (FIG. 5). There was no apparent inhibition of the alternate pathway tested with rabbit erythrocytes and EGTA. The mechanism of inhibition is undetermined but because C1q binds zsig37, C1 is the most likely target.

EXAMPLE 16

Inhibition by Zsig37 of Platelet Collagen Activation

Blood was drawn from healthy volunteers into tubes containing sodium citrate, maintained at room temperature and used within four hours of drawing. Whole blood was analyzed for platelet activation using a Chrono-Log 560A Whole Blood Lumi-Aggregometer (Chrono-Log Corp., Haverton, Pa.) according to manufacturer's instructions. For each test point, 500 μl of blood was added to a reaction tube containing a stir bar and 500 μl of isotonic saline containing zsig37 at concentrations from 0 to 20 μg/ml. The mixture was incubated for four minutes followed by platelet activation initiated by the addition of 5 μl of 1 mg/ml cross-linked collagen (Chrono-Log Corp.) to the blood/zsig37 mixture. Inhibition of activation by ADP (final concentration 10 μM), and thrombin (final concentration 1U/ml) was tested in a similar way.

Figure 6:
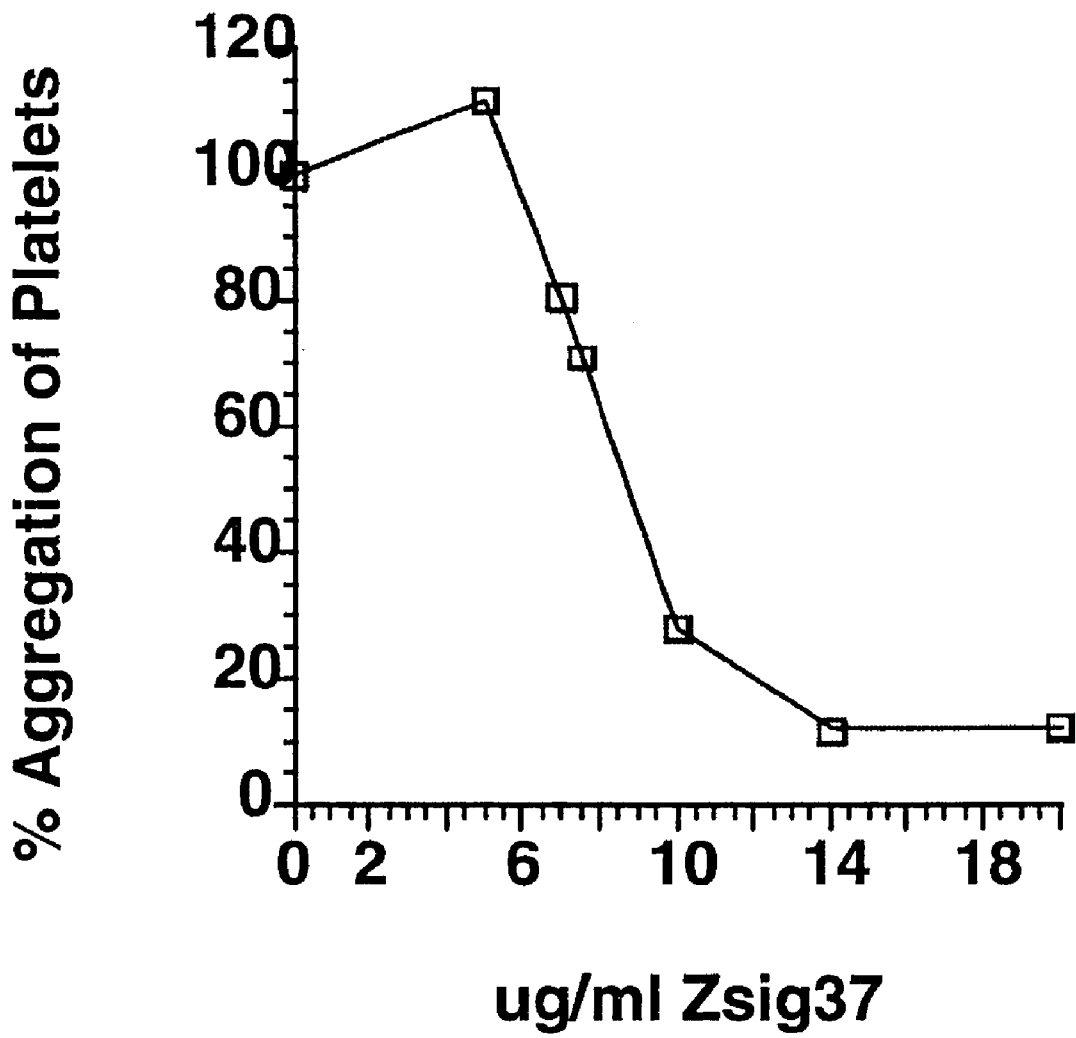
FIG. 6 shows the percent aggregation of platelets by collagen in the presence of zsig37.

Inhibition of collagen-mediated platelet activation by zsig37 shows a dose dependent relationship between 5 and 20 μg/ml (FIG. 6a). The inhibition is selective for collagen activation and has no effect on activation stimulated by ADP or thrombin (FIG. 6b). Collagen activation was not inhibited by another complement C1q related protein zsig39 (co-pending U.S. patent application Ser. No. 09/140,804).

EXAMPLE 17

Stimulation of SK5 Fibroblast Growth by Zsig37

Human fibronectin (25 ug/ml, GIBCO BRL, Gaithersburg, Md.) was plated into 96 well plates (Costar, Pleasanton, Calif.) at 100 μl/well and allowed to dry in a laminar hood overnight. Human SK5 fibroblasts in DMEM (Gibco) containing 10% Fetal Bovine Serum—low endotoxin (Hyclone, Logan, Utah) were plated at 5000 cells/well into the fibronectin-coated plates and incubated at 37° C., 5% $CO_2$ for 2 to 3 days. The number of cells per plate was adjusted to achieve non-confluence. Cells were then washed twice with serum-free DMEM hi glucose (Gibco) and serum starved by growing in serum-free DMEM hi glucose for 24 hours. Zsig37 was added to the wells in triplicate, at concentrations of 312.2 ng/ml to 10,000 ng/ml in 100 μl DMEM. The cells were then incubated for 48 hours at 37° C., 5% $CO_2$. Cell proliferation was tested by adding 15 μl MTT dye solution (CellTiter96™ kit, Promega) to each well. The plate was incubated 4 hours at 37° C., 5% $CO_2$ and the reaction was stopped with Solublization/Stop solution (CellTiter96™ kit, Promega) according to the manufacturer's instructions. The plate was incubated for 1 hour to solubilize formazan crystals and the absorbance was measured at 570 nm with a reference at 650 nm using an ELISA plate reader.

Figure 7:
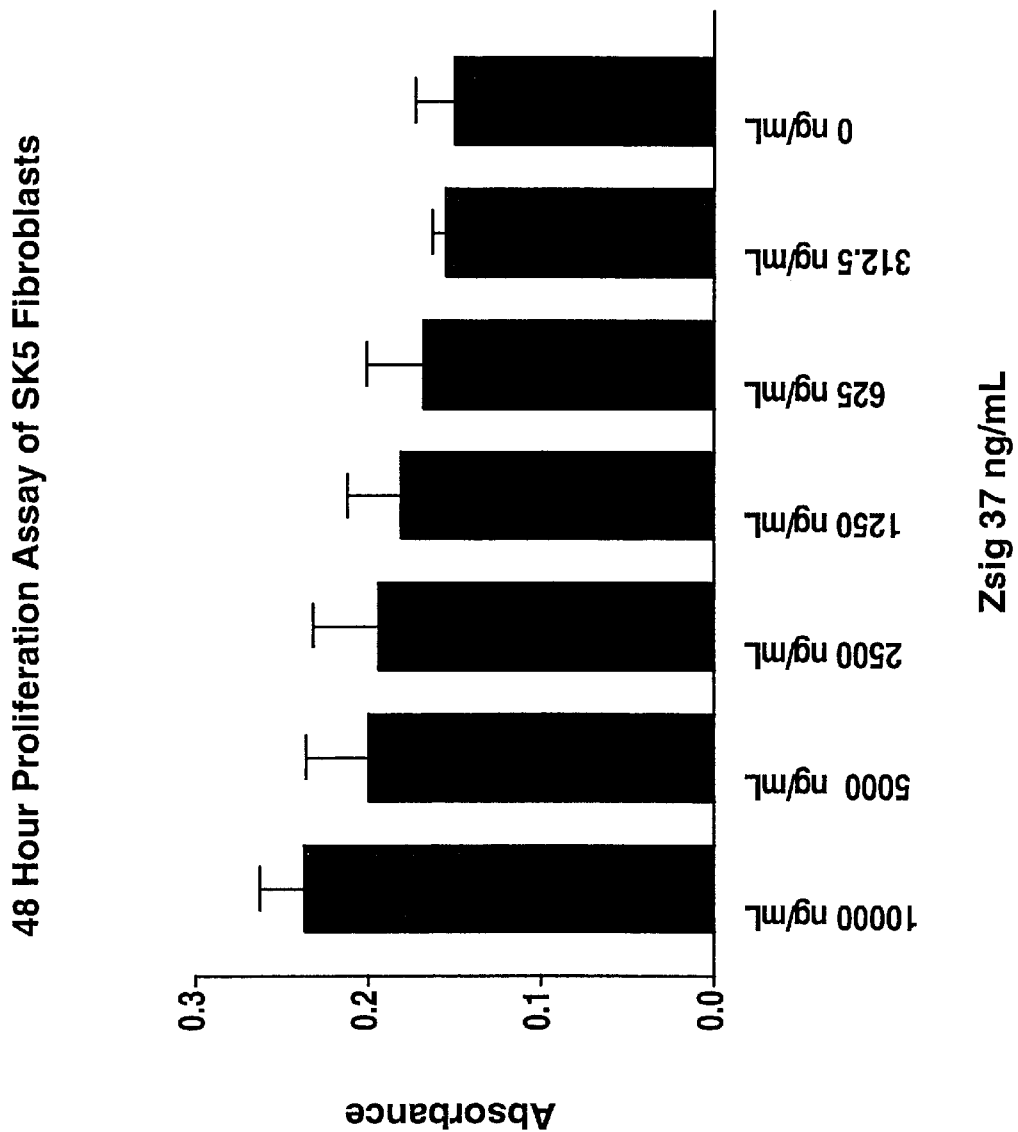
FIG. 7 shows proliferation of SK5 fibroblasts in the presence of zsig37.

The results (FIG. 7) show a dose dependent increase in SK5 fibroblast number over the range of zsig37 concentrations tested. These concentrations were within the range of values seen for the mitogenic effects of the fibrinogen b chain (Gray, et al, *Am J. Respir. Cell Mol. Biol.* 12, 684,1995 and Gray, et al, *J. Biol. Chem.* 270, 26602, 1995) and for fibroblast cell adhesion to plated C1q (Bordin, and Ghebrehiwet, *J. Immun.* 145:2520, 1990) both of which are believed to interact with cell surface calreticulin.

EXAMPLE 18

Zsiq37 Anti-Sera Production

Rabbit polyclonal anti-sera was prepared by immunizing two female New Zealand white rabbits with zsig37-CEE purified from BHK cells. The protein was conjugated to the carrier protein keyhole limpet hemocyanin (KLH) with gluteraldehyde. The rabbits were each given an initial intraperitoneal (ip) injection of 200 μg of peptide in Complete Freund's Adjuvant followed by booster ip injections of 100 μg peptide in Incomplete Freund's Adjuvant every three weeks. Seven to ten days after the administration of the second booster injection, the animals were bled and the serum was collected. The animals were then boosted and bled every three weeks.

EXAMPLE 19

Detection of FITC Tagged Zsiq37 Protein Binding in Tissues

FITC tagged Zsig37 protein binding in tissues was detected as follows:

Paraffin embedded and sectioned human tissues or mouse embryos on slides were obtained either from commercial sources (i.e. DAKO Corporation, Carpinteria, Calif.; BioGenex, San Ramon, Calif.; Novagen, Madison, Wis.; and Biomeda, Foster City, Calif.) or in house. The human tissue sections included adrenal gland, brain, heart, small intestine, large intestine, kidney, liver, lung, ovary, pancreas, prostate, spleen, stomach, testis, thyroid, and uterus. The mouse embryo sections were from the 16 day stage.

The tissue sections were dewaxed using standard conditions of 3×5 minutes in xylene, 4 minutes in 100% ethanol (EtOH), 3 minutes in 100% EtOH, and 2 minutes in 95% EtOH. The tissue sections were then subjected to a 20 minute antigen retrieval process at 94° C. according to the manufactures instructions (DAKO Corporation), followed by a 20 minute 0.01% Pepsin/0.2 N HCl digest. The tissue sections were rinsed twice in $dH_2O$ and once in PBS/0.05% Tween 20 (Sigma, St. Louis, Mo.) buffer and then blocked for 45 minutes with 1×PBS/5% BSA/5% nonfat dry milk (Carnation, Los Angeles, Calif.). This was followed by an avidin/biotin blocking step done according to the manufacturers instructions (Vector Laboratories, Inc., Burlingame, Calif.). The tissue sections were washed 3 times in 1×PBS/0.05% Tween 20 buffer and then incubated with appropriate concentration of FITC tagged Zsig37 protein in PBS/5% BSA for 45–60 minutes. After washing the tissue sections 3 times in 1×PBS/0.05% Tween 20, they were incubated with a 1:400 dilution of anti-FITC (mo) MAb Biotin conjugate (Sigma) for 30–60 minutes, washed 3 times in PBS/0.05% Tween 20 and then incubated for 30–60 minutes with a 1:500 dilution of Streptavidin-FITC (NEN Life Science Products, Boston, Mass.) followed by 2 washes in 1×PBS/0.05% Tween 20 buffer and 1 wash in 1×PBS without Tween 20. The tissues sections were then mounted with an antifade medium containing 0.5 $\mu$g/ml propidium iodode as counterstain.

Significant binding was seen to vessel walls and fine fibrous connective type tissues such as collagenous matrix in the majority of the human tissues and embryo sections studied.

EXAMPLE 20

Zsig37 in the Rabbit Carotid Artery Injury Model

Zsig37 was administered in a modified rabbit carotid artery injury model (Folts et al., *Circulation* 79:116–24, 1989 and Golino et al., *Thrombosis and Haemostasis* 67:302–5, 1992) to determine the degree of protection offered in preventing vascular occlusion following a crush injury.

Thirty four male New Zealand White rabbits, approximately 3–6 months old (R&R Rabbitry, Stanwood, Wash.) were into two groups. Fifteen rabbits received doses of zsig37 ranging from 2–13.5 $\mu$g/kg and 19 control rabbist were injected with PBS or equivalent amounts of PBS or zsig39, another adipocyte complement related protein (WO99/10492). The rabbits were anesthetized with ketamine (50 mg/kg, IM) and maintained on halothane inhalation anesthesia for the duration of the study. The hair was shaved from the ears and neck and an angiocatheter was placed in the marginal ear vein for IV support. A midline incision was made in the neck and the carotid artery was accessed. Approximately 5 cm of the common carotid artery proximal to the internal/external bifurcation was exposed via blunt dissection away from the surrounding tissue and any visible side branches were cauterized. A flow probe (Transonic Systems, Inc., Ithaca N.Y.) was placed distal to the anticipated injury site and a baseline blood flow was established. A 2.5–3.0 cm section of the vessel was then isolated from circulation using atraumatic vascular clamps. Following removal of the blood from the vessel segment, 0.4 ml of zsig37 in 0.9% sodium chloride or 0.04 ml 0.9% sodium chloride as a control, was injected into the empty vessel segment using a 30G needle. The vessel was left undisturbed for a 5 minute pre-injury treatment. A 1.0 cm crush injury was then inflicted into the center of the vessel segment using a guarded hemostat and left undisturbed for 10 minutes. The vessel clamps were then removed and blood flow reestablished. Blood flow was monitored continuously for 60 minutes after which time the rabbits were euthanized and the vessel excised for histological analysis.

No dose dependency was seen at these concentrations. A meta analysis of all zsig37 doses. resulted in significant increase in time patent when compared to controls in an unpaired t-test (P=0.019).

The mean percent time patent for the combined groups of negative control animals, as determined from blood flow tracings, was 13.5% with a standard error of ±1.7%. The mean percent time patent for the combined zsig37 treated groups of animals, as determined from blood flow tracings, was 37.2% with a standard error of ±10.3%.

In a second series of experiments, fluoresceinated zsig37 was used in the injured carotid artery model. Male, New Zealand White rabbits were anesthetized as above. Via an incision in the neck, the carotid artery was exposed and approximately 5 cm of the vessel isolated from the surrounding consecutive tissue. Blood was evacuated from the isolated segment and atraumatic vascular clips were applied. Approximately 0.05 ml of fluoreceinated zsig37 (concentration 100 $\mu$g/ml) was injected into the isolated segment to completely fill the vessel using a 30 g needle. After an exposure period of 5 minutes, the vessel was injured and the exposure continued for another 110 minutes before the clips were removed and blood flow reestablished. The animals were euthanized as described above at 1, 10, and 60 minutes post-reestablishment of blood flow and the vessels collected and formalin fixed for histological evaluation.

Labeled zsig37 preferentially bound to receptors in the media of the injured vessels. Labeled zsig37 did not bind to areas of the vessel that were uninjured. The time of blood flow prior to vessel collection does not appear to effect the amount of zsig37 that remains bound to the tissue, i.e., there was no difference in the amount of labeled zsig37 bound to the tissues in the 1 minute vs. the 60 minute collection time point. This may indicate that zsig37 tightly binds to the injured vessel and is not washed off by the reestablished blood flow.

The effect of zsig37 on blood flow dynamics following vascular injury in a rabbit iliac artery crush injury/stenosis model was also evaluated. Young adult male New Zealand White rabbits were anesthetized as described above. Via an abdominal incision, the aorto-iliac bifurcation was exposed and each iliac freed of surrounding tissues and the main branches ligated. Each iliac was instrumented with an ultrasound flow probe to monitor blood flow through the vessel. Based on blood flow data, one iliac was selected to be used for the injury and the other was catheterized for delivery of the test sample. Rabbits were divided into dose groups of 6 animals/group. Test sample doses containing zsig37 increased in half-log increments from 3–1000 $\mu$g/kg over the selected infusion period. The test samples infusion was initiated followed by creation of a critical stenosis that reduced blood flow through the vessel by approximately 50%. After creation of the stenosis and a period of blood flow stabilization, the vessel was injured by crushing the vessel between the jaws of a smooth needle holder. The infusion was continued post-injury for a set period of time, 10–20 minutes. Blood flow through the injured vessel was monitored for 60 minutes post-injury. The animals were euthanized at he conclusion of the study period. The lower section of the abdominal aorta and each iliac were collected and formalin fixed for histological evaluation.

Blood flow parameters determined from the flow tracings, included mean flow post-stenosis, mean flow post-injury, and time the vessel remained patent. This data suggests there is a tendency for zsig37 to promote increased patency time with increased dose up to 300 $\mu$g/kg/ over a 60 minute period.

EXAMPLE 21

Relaxation of Serotonin-induced Rat Aortic Ring Contractions

Male, Sprague-Dawley rats, approximately 3 months of age, were lightly anesthetized with $CO_2$ and then decapitated. The thoracic aorta was then rapidly removed and placed in a modified Kreb's-Henseleit buffer (NaCl, 118.2 mM; KCl, 4.6 mM; $CaCl_2$, 2.5 mM; $MgSO_4$, 1.2 mM; $NaHCO_3$, 24.8 mM; $KH_2PO_4$, 1.2 mM; and glucose, 10.0 mM). From each rat, four 2–3 mm aortic ring sections were cut after discarding the rough end of the aorta. In some experiments the endothelium was denuded, prior to cutting ring sections, by rubbing the lumen of the aorta along a 21 gauge needle. Denudation of the endothelium was verified by the addition of the acetylcholine analogue, carbachol, prior to determining zsig37 concentration-dependent responses. In the absence of the endothelium, carbachol does not vasorelax constricted vascular ring sections.

The rings were fixed and connected to force displacement transducers in oxygenated (95% $O_2$, 5% $CO_2$), jacketed, glass organ baths kept at 30° C. in modified Kreb's-Henseleit buffer, pH 7.4. Resting tension was set at 1 gm, and continually re-adjusted to 1 gm over a 1 hour incubation period. Fresh oxygenated modified Kreb's-Henseleit buffer was added to the baths every fifteen minutes during the resting incubation period. At the end of the 1 hour incubation, the ring sections were contracted by the addition of 10 μM serotonin. After maximum contraction had been reached, approximately 15–20 minutes after the addition of the serotonin, cumulative concentration response curves for zsig37 were constructed. Zsig37 was added to 5 ml baths in volumes from 5 up to 150 μls, for final concentrations ranging from 1 ng/ml up to 40 μg/ml. Viability of the ring sections was verified at the end of the concentration response by the addition of forskolin (2.5 μM or 25 μM) or nitroglycerin (22 μM).

Addition of zsig37 induced a concentration-dependent vasorelaxation of serotonin-contracted rat aortic sections with and without an intact endothelium. Relaxation in response of zsig37 was first observed at concentrations above 100 ng/ml. Relaxation was observed approximately 30–60 seconds after the additions of each zsig37 concentration to the bath, and relaxation responses plateaued within 3–5 minutes after the addition of zsig37. The character of the relaxation response to zsig37 indicates that the vasorelaxation is a receptor-second messenger mediated event. Additionally, the ability of zsig37 to vasorelax endothelium-denuded aortic sections indicates that zsig37 acts directly on the smooth muscle cells to elicit the vasorelaxant response.

EXAMPLE 22

Identification of Cells Expressing zsiq37 Receptor Using in Situ Hybridization Specific human tissues were isolated and screened for zsig37 expression by in situ hybridization. Various human tissues prepared, sectioned and subjected to in situ hybridization included aorta, heart, lymph node, placenta. Prostate, salivary gland, skin, and testis. The tissues were fixed in 10% buffered formalin (Surgipath, Richmond, Ill.), and embedded in parapalst X-tra (Oxford Scientific, St. Louis, Mo.), and sectioned at 5 μm with a Reichart-Jung 2050 microtome (Leica Instruments GmbH, Nussloch, Germany). Tissues were sectioned at 4 to 8 microns. Tissues were prepared using a standard protocol ("Development of nono-isopotic in situ hybridization", Laboratory of Experimental Pathology, National Institute of Environmental Health Sciences, Research Park Triangle, N.C.). Briefly, tissue sections were deparaffinized with HistoClear (National Diagnostics, Atlanta, Ga.) and then dehydrated with ethanol. Next the sections were digested with Proteinase K (50 μg/ml) (Boehringer Mannheim, Indianapolis, Ind.) at 37° C. for 2 to 20 minutes. This step was followed by acetylation and re-hydration of the tissues.

Three in situ probes generated by PCR were designed against the human zsig37 sequence. Two sets of oligonucleotide primers were designed to generate probes for separate regions of the zsig37 cDNA: (1) Oligonucleotide ZC23,689 (SEQ ID NO:45) and ZC23,694 (SEQ ID NO:46) were used to generate a 414 bp probe for zsig37; (2) ZC23,703 (SEQ ID NO:47) and ZC23,697 (SEQ ID NO:48) were used to generate a 896 bp probe for zsig37; (3) ZC24,441 (SEQ ID NO:49) and ZC24,442 (SEQ ID NO:50) were used to generate a 290 bp probe for zsig37. The antisense oligo from each set also contained the working sequence for the T7 RNA polymerase promoter to allow for easy transcription of antisense RNA probes from these products. The PCR products were purified by Qiagen spin columns (Qiagen, Inc., Chatsworth, Calif.) followed by phenol/chloroform extraction and ethanol precipitation. Probes were subsequently labeled with digoxigenin (Boehringer) or biotin (Boehringer) using an in vitro transcription system (Promega Corp., Madison, Wis.) according to the manufacturer's instructions.

In situ hybridization was performed with a digoxigenin- or biotin-labeled zsig37 probe as described above. The probe was added to the slides at a concentration of 1 to 5 pmol/ml for 12 to 16 hours at 50–60° C. Slides were subsequently washed in 2×SSC and 0.1×SSC at 50–55° C. Slides were subsequently washed in 2×SSC and 0.1×SSC at 50–55° C. The signals were amplified using tyramide signal amplification (TSA in situ indirect kit, NEN, Boston, Mass.) and visualized with a Vector Red substrate kit (Vector Laboratories, Burlingame, Calif.) according to manufacturer's instructions. The slides were then counter-stained with hematoxylin (Vector Laboratories).

Positive signals were seen in the human aorta, heart, prostate, salivary gland, and testis. The positive-staining cells appeared to be endothelial cells of small diameter vessels in the advantitia surrounding the aorta, mesothelial cells overlying the epicardium, acinar cells of the salivary gland and scattered mononuclear cells, trophoblasts of the placenta, epithelial cells of the prostate and stratified epithelium of the seminiferous tubules of testis.

EXAMPLE 23

SEC-MALLS Analysis of Zsig37

Zsig37 contains a N-terminal collagen-like domain as well as a C-terminal globular region having homology to the tumor necrosis factor family and like other such proteins, zsig37 is expected to multimerize. Purified zsig37 analyzed using an ESI-ion trap mass spectrometer (Finnigan Matt, San Jose, Calif.) indicated the presence of species approximating trimers and 9 mers, which was an unexpected result when compared to other homologous proteins. Peptide mapping of zsig37 using LC-MS/MS on an ESI-ion trap mass spectrometer (Finnigan Matt) revealed that several cysteine residues were modified with an S-cysteinyl group. It may be that modification of key cysteine residues in the zsig37 protein during fermentation with free cysteine in the media is preventing proper oligomeric association of this molecule.

To learn more, a comparison of reduced and nonreduced zsig37 was made using a Biosep S-300 size exclusion column at 1.0 ml/minute (7.8×3000 mm; Phenomenex, Torrance, Calif.) on a HP 1050 HPLC (Hewlett Packard, Heidleberg, Germany). The HP 1050 was coupled to light scattering and refractive index detectors, miniDAWN and Optilab DSP, (Waytt Technology, Santa Barbara, Calif.) for on-line SEC-MALLS.

One milligram of recombinant zsig37 (1.0 mg/ml) was added to TCEP at a 10:1 mol/mol ratio of TCEP to zsig37 and kept at room temperature for 70 minutes. Sixty microliters of the reduced zsig37 was injected for SEC-MALLS analysis and the remainder of the reduced zsig37 was dialyzed in 0.5–3.0 ml Slide-A-Lyzer cassettes, 10K MWCO (Pierce, Rockford, Ill.) with stirring against PBS, pH 7.4 with three buffer changes as follows: 1 liter PBS at room temperature for 4 hours, 1 liter PBS at 4° C. overnight, and 1 liter PBS at room temperature for 4 hours.

Following dialysis, oxidation was allowed to continue at 4° C. The oxidation was monitored by SEC-MALLS analysis of aliquots taken at three time points, T=0 hours, T=24 hours, and T=96 hours. Molecular weight values were determined using the LS-RI, two-detector method.

Analysis of the reduced, dialyzed recombinant zsig37 seems to initially indicate the formation of hexamers and 18 mers as detected by SEC-MALLS which is more consistent with the oligomeric states observed in homologs. These forms were also active in in vitro assays.

EXAMPLE 24

Zsiq37 Binding to Monocytes

CD14 positive monocytes were isolated from frozen peripheral blood aphaeresis product using a positive selection method with Miltenyi beads (Miltenyi Biotec Auburn, Calif.). Purified cells were greater than 80% CD14 positive via FACS staining. Cells were resuspended at 1×10$^6$ cells/ml in RPMI+10% fetal bovine serum (FBS) and plated in 100 mm tissue culture dishes, 5 ml/plate. Recombinant human γ interferon was added at 100 ng/ml and the cells were incubated at 5% $CO_2$, 37° C. for 48 hours.

The cells were removed from the plates by nonenzymatic methods using both EDTA and scraping, concentrated by centrifugation, resuspended in FACS staining buffer and aliquoted at 500,000 cells/tube for staining. Nonactivated cells were obtained by performing another CD14 selection with the same apheresis product post 48 hours in γ interferon. The cells were incubated in varying concentrations of biotinylated zsig37 followed by Streptavidin PE. All blocking with "cold" zsig37 was done on ice for 30 minutes. Unbound protein was removed by washing once in FACS buffer. Binding was quantitated using a FACS caliber instrument (Becton Dickinson, Lincoln Park, N.J.) and expressed as a signal above secondary antibody only control. Monocyte activation was verified by approximately a 1 log increase in ICAM-1 expression in γ interferon treated cells.

Zsig37 binding was detected in both activated and non-activated monocytes, with an increase in zsig37 binding observed in γ interferon-treated cells. Binding was detected down to 1.5 μg/ml, the lowest concentration tested. At 15 μg/ml, binding was approximately 4 fold increased in activated cells. A slight (approximately 10%) reduction in binding was seen in activated cells only when pretreated with 70 fold excess "cold" zsig37. Increased zsig37 binding in activated monocytes suggests that the up-regulation of monocyte binding proteins/receptors for zsig37 by inflammatory cytokines. This could potentially result in zsig37 involvement in monocyte phagocytosis, microbial killing, and cellular cytotoxicity. Following the two days in culture, there are macrophages present in the culture and zsig37 may be binding preferentially to this subset of cells. There are no good macrophage markers available to determine if this is occurring. Zsig37 also bound to a mouse monocyte/macrophage line, RAW 264.7 (ATCC No. CRL-2278), indicating macrophage specificity.

EXAMPLE 25

Indium Labeled zsiq37

A ten-fold molar excess of DTPA (diethylenetriamine pentaacetic acid), a chelating agent, was reacted with zsig37. The resultant product was delivered into a 10,000 MWCO Slide-A-Lyzer dialysis cassette, equilibrated in a 0.1 M Hepes buffer, pH 7.0 for a minimum of 4 hours or overnight, with at least one buffer exchange. The zsig 37/DTPA was removed from the cassette and reacted with $^{111}$In at 150 μCi/mg at room temperature for 30 minutes with rocking. The zsig37/$^{111}$In product was desalted to remove any unbound $^{111}$In and Hepes buffer using a PD-10 column equilibrated with 0.1 M Acetate pH 6.0, or 120 mM NaCl. Five hundred microliter fractions were collected and monitored for radioactivity on a gamma counter. The fractions containing protein (radiation) were pooled and 500 mM Na Phosphate pH 7.4 was added to the pooled volume to a final concentration of 10 mM.

$^{111}$In-labeled zsig37 was administered at 30, 100, 300 and 1000 μg/kg in a modified rabbit carotid artery injury model as described above. $^{111}$In-labeled zsig37 was detected in the highest concentrations at the site of the injury and in liver and kidney.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for minimizing vascular occlusion in a mammal, comprising administering to the mammal a therapeutically effective amount of a pharmaceutical formulation that comprises a pharmaceutically acceptable vehicle and an adipocyte complement related protein, wherein the adipocyte complement related protein has an amino acid sequence comprising amino acid residues 26 to 281 of SEQ ID NO:2, and wherein administration of the pharmaceutical formulation promotes blood flow.

2. The method of claim 1, wherein the adipocyte complement related protein has an amino acid sequence comprising amino acid residues 22 to 281 of SEQ ID NO:2.

3. The method of claim 1, wherein the adipocyte complement related protein has an amino acid sequence comprising amino acid residues 1 to 281 of SEQ ID NO:2.

4. The method of claim 1, wherein the adipocyte complement related protein is administered concurrently with, or before, an acute vascular injury.

5. The method of claim 1, wherein the adipocyte complement related protein is administered following an acute vascular injury.

6. The method of claim 1, wherein blood flow is increased by inhibiting at least one event selected from the group consisting of: inhibition of collagen-mediated platelet adhesion, inhibition of collagen-mediated platelet activation, and inhibition of collagen-mediated platelet aggregation.

7. The method of claim 1, wherein the pharmaceutical formulation comprises a complex of oligomerized adipocyte complement related proteins.

8. The method of claim 7, wherein the adipocyte complement related proteins of the complex are bound to each other by intermolecular disulfide bonds.

9. The method of claim 7, wherein the pharmaceutical formulation comprises a trimer of adipocyte complement related proteins.

10. The method of claim 7, wherein the pharmaceutical formulation comprises a hexamer of adipocyte complement related proteins.

11. The method of claim 7, wherein the pharmaceutical formulation comprises an 18 mer of adipocyte complement related proteins.

12. A method for minimizing vascular occlusion in a mammal, comprising administering to the mammal a therapeutically effective amount of a pharmaceutical formulation that comprises a pharmaceutically acceptable vehicle and adipocyte complement related proteins that have an amino acid sequence comprising amino acid residues 1 to 281 of SEQ ID NO:2, wherein the adipocyte, complement related proteins are oligomerized to form a complex selected from the group consisting of trimer, hexamer, and 18 mer, and wherein administration of the pharmaceutical formulation promotes blood flow.

13. A method for inducing vasodilation within the vasculature of a mammal, comprising administering to the mammal a therapeutically effective amount of a pharmaceutical formulation that comprises a pharmaceutically acceptable vehicle and an adipocyte complement related protein, wherein the adipocyte complement related protein has an amino acid sequence comprising amino acid residues 26 to 281 of SEQ ID NO:2, and wherein administration of the pharmaceutical formulation elicits a vasorelaxant response.

14. The method of claim 13, wherein the adipocyte complement related protein has an amino acid sequence comprising amino acid residues 22 to 281 of SEQ ID NO:2.

15. The method of claim 13, wherein the adipocyte complement related protein has an amino acid sequence comprising amino acid residues 1 to 281 of SEQ ID NO:2.

16. The method of claim 13, wherein the pharmaceutical formulation comprises a complex of oligomerized adipocyte complement related proteins.

17. The method of claim 16, wherein the adipocyte complement related proteins of the complex are bound to each other by intermolecular disulfide bonds.

18. The method of claim 16, wherein the pharmaceutical formulation comprises a trimer of adipocyte complement related proteins.

19. The method of claim 16, wherein the pharmaceutical formulation comprises a hexamer of adipocyte complement related proteins.

20. The method of claim 16, wherein the pharmaceutical formulation comprises an 18 mer of adipocyte complement related proteins.

21. A method for inducing vasodilation within the vasculature of a mammal, comprising administering to the mammal a therapeutically effective amount of a pharmaceutical formulation that comprises a pharmaceutically acceptable vehicle and adipocyte complement related proteins that have an amino acid sequence comprising amino acid residues 1 to 281 of SEQ ID NO:2, wherein the adipocyte complement related proteins are oligomerized to form a complex selected from the group consisting of trimer, hexamer, and 18 mer, and wherein administration of the pharmaceutical formulation elicits a vasorelaxant response.

\* \* \* \* \*

SEQUENCE LISTING

<160> NUMBER OF SEQ ID NOS: 55

<210> SEQ ID NO 1
<211> LENGTH: 2769
<212> TYPE: DNA
<213> ORGANISM: Homo sapiens
<220> FEATURE:
<221> NAME/KEY: CDS
<222> LOCATION: (171)...(1013)

<400> SEQUENCE: 1

-continued

```
gaattcgaat tcctttgttt ccactgggac ggaatcggag ctctggaggc tgggctggcc        60
aagcgccccg aaggcccgat gcctgacggc tcatgcggcc tccttgtttg cagggcctgg       120
gcaaaaattt acactgagtc ccactcttcg ctccagggcc cggcaggaag atg ggc         176
                                                      Met Gly
                                                        1 tcc cgt gga cag gga ctc ttg ctg gcg tac tgc ctg ctc ctt gcc ttt        224
Ser Arg Gly Gln Gly Leu Leu Leu Ala Tyr Cys Leu Leu Leu Ala Phe
        5                  10                  15 gcc tct ggc ctg gtc ctg agt cgc gtg ccc cat gtc cag ggg gaa cag        272
Ala Ser Gly Leu Val Leu Ser Arg Val Pro His Val Gln Gly Glu Gln
 20                  25                  30 cag gag tgg gag ggg act gag gag ctg ccg tcc cct ccg gac cat gcc        320
Gln Glu Trp Glu Gly Thr Glu Glu Leu Pro Ser Pro Pro Asp His Ala
 35                  40                  45                  50 gag agg gct gaa gaa caa cat gaa aaa tac agg ccc agt cag gac cag        368
Glu Arg Ala Glu Glu Gln His Glu Lys Tyr Arg Pro Ser Gln Asp Gln
                 55                  60                  65 ggg ctc cct gct tcc cgg tgc ttg cgc tgc tgt gac cct ggt acc tcc        416
Gly Leu Pro Ala Ser Arg Cys Leu Arg Cys Cys Asp Pro Gly Thr Ser
                 70                  75                  80 atg tac ccg gcg acc gcc gtg ccc cag atc aac atc act atc ttg aaa        464
Met Tyr Pro Ala Thr Ala Val Pro Gln Ile Asn Ile Thr Ile Leu Lys
             85                  90                  95 ggg gag aag ggt gac cgc gga gat cga ggc ctc caa ggg aaa tat ggc        512
Gly Glu Lys Gly Asp Arg Gly Asp Arg Gly Leu Gln Gly Lys Tyr Gly
100                 105                 110 aaa aca ggc tca gca ggg gcc agg ggc cac act gga ccc aaa ggg cag        560
Lys Thr Gly Ser Ala Gly Ala Arg Gly His Thr Gly Pro Lys Gly Gln
115                 120                 125                 130 aag ggc tcc atg ggg gcc cct ggg gag cgg tgc aag agc cac tac gcc        608
Lys Gly Ser Met Gly Ala Pro Gly Glu Arg Cys Lys Ser His Tyr Ala
                135                 140                 145 gcc ttt tcg gtg ggc cgg aag aag ccc atg cac agc aac cac tac tac        656
Ala Phe Ser Val Gly Arg Lys Lys Pro Met His Ser Asn His Tyr Tyr
                150                 155                 160 cag acg gtg atc ttc gac acg gag ttc gtg aac ctc tac gac cac ttc        704
Gln Thr Val Ile Phe Asp Thr Glu Phe Val Asn Leu Tyr Asp His Phe
            165                 170                 175 aac atg ttc acc ggc aag ttc tac tgc tac gtg ccc ggc ctc tac ttc        752
Asn Met Phe Thr Gly Lys Phe Tyr Cys Tyr Val Pro Gly Leu Tyr Phe
180                 185                 190 ttc agc ctc aac gtg cac acc tgg aac cag aag gag acc tac ctg cac        800
Phe Ser Leu Asn Val His Thr Trp Asn Gln Lys Glu Thr Tyr Leu His
195                 200                 205                 210 atc atg aag aac gag gag gag gtg gtg atc ttg ttc gcg cag gtg ggc        848
Ile Met Lys Asn Glu Glu Glu Val Val Ile Leu Phe Ala Gln Val Gly
                215                 220                 225 gac cgc agc atc atg caa agc cag agc ctg atg ctg gag ctg cga gag        896
Asp Arg Ser Ile Met Gln Ser Gln Ser Leu Met Leu Glu Leu Arg Glu
                230                 235                 240 cag gac cag gtg tgg gta cgc ctc tac aag ggc gaa cgt gag aac gcc        944
Gln Asp Gln Val Trp Val Arg Leu Tyr Lys Gly Glu Arg Glu Asn Ala
            245                 250                 255 atc ttc agc gag gag ctg gac acc tac atc acc ttc agt ggc tac ctg        992
Ile Phe Ser Glu Glu Leu Asp Thr Tyr Ile Thr Phe Ser Gly Tyr Leu
260                 265                 270 gtc aag cac gcc acc gag ccc tagctggccg gccacctcct ttcctctcgc          1043
Val Lys His Ala Thr Glu Pro
```

-continued

```
                  275                 280 cacctccac  ccctgcgctg  tgctgacccc  agggctcagc  accaggctga  ccccaccgcc    1103
tcttccccga  tccctggact  ccgactccct  ggctttggca  ttcagtgaga  cgccctgcac    1163
acacagaaag  ccaaagcgat  cggtgctccc  agatcccgca  gcctctggag  agagctgacg    1223
gcagatgaaa  tcaccagggc  ggggcacccg  cgagaaccct  ctgggacctt  ccgcggccct    1283
ctctgcacac  atcctcaagt  gaccccgcac  ggcgagacgc  gggtggcggc  agggcgtccc    1343
agggtgcggc  accgcggctc  cagtccttgg  aaataattag  gcaaattcta  aaggtctcaa    1403
aaggagcaaa  gtaaaccgtg  gaggacaaag  aaaagggttg  ttattttgt   ctttccagcc    1463 agcctgctgg  ctcccaagag  agaggccttt  tcagttgaga  ctctgcttaa  gagaagatcc    1523
aaagttaaag  ctctggggtc  agggagggg   ccggggcag   gaaactacct  ctggcttaat    1583
tcttttaagc  cacgtaggaa  ctttcttgag  ggataggtgg  accctgacat  ccctgtggcc    1643
ttgcccaagg  gctctgctgg  tctttctgag  tcacagctgc  gaggtgatgg  gggctggggc    1703
cccaggcgtc  agcctcccag  agggacagct  gagcccctg   ccttggctcc  aggttggtag    1763
aagcagccga  agggctcctg  acagtggcca  gggacccctg  ggtcccccag  gcctgcagat    1823
gtttctatga  ggggcagagc  tcctggtaca  tccatgtgtg  gctctgctcc  acccctgtgc    1883
caccccagag  ccctgggggg  tggtctccat  gcctgccacc  ctggcatcgg  ctttctgtgc    1943
cgcctcccac  acaaatcagc  cccagaaggc  cccggggctt  tggcttctgt  tttttataaa    2003
acacctcaag  cagcactgca  gtctcccatc  tcctcgtggg  ctaagcatca  ccgcttccac    2063
gtgtgttgtg  ttggttggca  gcaaggctga  tccagacccc  ttctgccccc  actgccctca    2123
tccaggcctc  tgaccagtag  cctgagaggg  gcttttttcta ggcttcagag  caggggagag    2183
ctggaagggg  ctagaaagct  cccgcttgtc  tgtttctcag  gctcctgtga  gcctcagtcc    2243
tgagaccaga  gtcaagagga  agtacacatc  ccaatcaccc  gtgtcaggat  tcactctcag    2303
gagctgggtg  gcaggagagg  caatagcccc  tgtggcaatt  gcaggaccag  ctggagcagg    2363
gttgcggtgt  ctccgcggtg  ctctcgccct  gcccatggcc  accccagact  ctgatctcca    2423
ggaaccccat  agccctctc   cacctcaccc  catgttgatg  cccagggtca  ctcttgctac    2483
ccgctgggcc  cccaaacccc  cgctgcctct  cttccttccc  cccatccccc  acctggtttt    2543
gactaatcct  gcttccctct  ctgggcctgg  ctgccgggat  ctggggtccc  taagtccctc    2603
tctttaaaga  acttctgcgg  gtcagactct  gaagccgagt  tgctgtgggc  gtgcccggaa    2663
gcagagcgcc  acactcgctg  cttaagctcc  cccagctctt  tccagaaaac  attaaactca    2723
gaattgtgtt  ttcagcaaaa  aaaaaaaaaa  aaaaaagggc  ggccgc                   2769
```

<210> SEQ ID NO 2
<211> LENGTH: 281
<212> TYPE: PRT
<213> ORGANISM: Homo sapien

<400> SEQUENCE: 2

```
Met Gly Ser Arg Gly Gln Gly Leu Leu Leu Ala Tyr Cys Leu Leu Leu
 1               5                  10                  15

Ala Phe Ala Ser Gly Leu Val Leu Ser Arg Val Pro His Val Gln Gly
            20                  25                  30

Glu Gln Gln Glu Trp Glu Gly Thr Glu Glu Leu Pro Ser Pro Pro Asp
        35                  40                  45

His Ala Glu Arg Ala Glu Glu Gln His Glu Lys Tyr Arg Pro Ser Gln
    50                  55                  60
```

Asp Gln Gly Leu Pro Ala Ser Arg Cys Leu Arg Cys Cys Asp Pro Gly
65                  70                  75                  80

Thr Ser Met Tyr Pro Ala Thr Ala Val Pro Gln Ile Asn Ile Thr Ile
                85                  90                  95

Leu Lys Gly Glu Lys Gly Asp Arg Gly Asp Arg Gly Leu Gln Gly Lys
            100                 105                 110

Tyr Gly Lys Thr Gly Ser Ala Gly Ala Arg Gly His Thr Gly Pro Lys
        115                 120                 125

Gly Gln Lys Gly Ser Met Gly Ala Pro Gly Glu Arg Cys Lys Ser His
    130                 135                 140

Tyr Ala Ala Phe Ser Val Gly Arg Lys Lys Pro Met His Ser Asn His
145                 150                 155                 160

Tyr Tyr Gln Thr Val Ile Phe Asp Thr Glu Phe Val Asn Leu Tyr Asp
                165                 170                 175

His Phe Asn Met Phe Thr Gly Lys Phe Tyr Cys Tyr Val Pro Gly Leu
            180                 185                 190

Tyr Phe Phe Ser Leu Asn Val His Thr Trp Asn Gln Lys Glu Thr Tyr
        195                 200                 205

Leu His Ile Met Lys Asn Glu Glu Val Val Ile Leu Phe Ala Gln
    210                 215                 220

Val Gly Asp Arg Ser Ile Met Gln Ser Gln Ser Leu Met Leu Glu Leu
225                 230                 235                 240

Arg Glu Gln Asp Gln Val Trp Val Arg Leu Tyr Lys Gly Glu Arg Glu
                245                 250                 255

Asn Ala Ile Phe Ser Glu Glu Leu Asp Thr Tyr Ile Thr Phe Ser Gly
            260                 265                 270

Tyr Leu Val Lys His Ala Thr Glu Pro
        275                 280

<210> SEQ ID NO 3
<211> LENGTH: 247
<212> TYPE: PRT
<213> ORGANISM: Homo sapien

<400> SEQUENCE: 3

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
            20                  25                  30

Pro Pro Pro Lys Gly Thr Cys Ala Gly Trp Met Ala Gly Ile Pro Gly
        35                  40                  45

His Pro Gly His Asn Gly Thr Pro Gly Arg Asp Gly Arg Asp Gly Thr
    50                  55                  60

Pro Gly Glu Lys Gly Glu Lys Gly Asp Ala Gly Leu Leu Gly Pro Lys
65                  70                  75                  80

Gly Glu Thr Gly Asp Val Gly Met Thr Gly Ala Glu Gly Pro Arg Gly
                85                  90                  95

Phe Pro Gln Thr Pro Gly Arg Lys Gly Glu Pro Gly Glu Ala Ala Tyr
            100                 105                 110

Met Tyr Arg Ser Ala Phe Ser Val Gly Leu Glu Thr Arg Val Thr Val
        115                 120                 125

Pro Asn Val Pro Ile Arg Phe Thr Lys Ile Phe Tyr Asn Gln Gln Asn
    130                 135                 140

His Tyr Asp Gly Ser Thr Gly Lys Phe Tyr Cys Asn Ile Pro Gly Leu

```
                    145                 150                 155                 160
Tyr Tyr Phe Ser Tyr His Ile Thr Val Tyr Met Lys Asp Val Lys Val
                165                 170                 175
Ser Leu Phe Lys Lys Asp Lys Ala Val Leu Phe Thr Tyr Asp Gln Tyr
            180                 185                 190
Gln Glu Lys Asn Val Asp Gln Ala Ser Gly Ser Val Leu Leu His Leu
        195                 200                 205
Glu Val Gly Asp Gln Val Trp Leu Gln Val Tyr Gly Asp Gly Asp His
    210                 215                 220
Asn Gly Leu Tyr Ala Asp Asn Val Asn Asp Ser Thr Phe Thr Gly Phe
225                 230                 235                 240
Leu Leu Tyr His Asp Thr Asn
                245

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide ZC12447

<400> SEQUENCE: 4
atggggcacg cgactcagga ccaggccaga                                         30

<210> SEQ ID NO 5
<211> LENGTH: 19
<212> TYPE: DNA
<213> ORGANISM: Artificial Sequence
<220> FEATURE:
<223> OTHER INFORMATION: Oligonucleotide ZC695

<400> SEQUENCE: 5
gatttaggtg acactatag                                                    19

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide ZC694

<400> SEQUENCE: 6
taatacgact cactataggg                                                   20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide ZC13210

<400> SEQUENCE: 7
aagcaccggg aagcagggag                                                   20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide ZC13588

<400> SEQUENCE: 8
cgggcacgta gcagtagaac                                                   20
```

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide ZC13532

<400> SEQUENCE: 9
gagagggctg aagaacaaca                                         20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide ZC13641

<400> SEQUENCE: 10
aaggtggcga gaggaaagga                                         20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide ZC13586

<400> SEQUENCE: 11
tgttcaccgg caagttctac                                         20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide ZC13651

<400> SEQUENCE: 12
ctttgtcctc cacggtttac                                         20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide ZC13622

<400> SEQUENCE: 13
tttcctctcg ccaccttcca                                         20

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide ZC13625

<400> SEQUENCE: 14
cttcggctgc ttctaaccaa c                                       21

<210> SEQ ID NO 15
<211> LENGTH: 20
<212> TYPE: DNA
<213> ORGANISM: Artificial Sequence
<220> FEATURE:

-continued

<223> OTHER INFORMATION: Oligonucleotide ZC13650

<400> SEQUENCE: 15
gtaaaccgtg gaggacaaag                                                    20

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide ZC13859

<400> SEQUENCE: 16
gctgccaacc aacacaacca c                                                  21

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide ZC13624

<400> SEQUENCE: 17
gcaggattag tcaaaacc                                                      18

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide ZC13531

<400> SEQUENCE: 18
aacatggggt gaggtggaga                                                    20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide ZC13587

<400> SEQUENCE: 19
tcctcgtggg ctaagcatca                                                    20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide ZC13623

<400> SEQUENCE: 20
atctccagga accccatagc                                                    20

<210> SEQ ID NO 21
<211> LENGTH: 18
<212> TYPE: DNA
<213> ORGANISM: Artificial Sequence
<220> FEATURE:
<223> OTHER INFORMATION: Oligonucleotide ZC14444

<400> SEQUENCE: 21
tctccaggaa ccccatag                                                      18

<210> SEQ ID NO 22
<211> LENGTH: 18
<212> TYPE: DNA
<213> ORGANISM: Artificial Sequence
<220> FEATURE:
<223> OTHER INFORMATION: Oligonucleotide ZC14445

<400> SEQUENCE: 22
gcaggattag tcaaaacc                                                       18

<210> SEQ ID NO 23
<211> LENGTH: 843
<212> TYPE: DNA
<213> ORGANISM: Artificial Sequence
<220> FEATURE:
<223> OTHER INFORMATION: Degenerate nucleotide sequence encoding zsig37
      polypeptide
<221> NAME/KEY: variation
<222> LOCATION: (1)...(843)
<223> OTHER INFORMATION: Each N is independently any nucleotide.

<400> SEQUENCE: 23
atgggnwsnm gnggncargg nytnytnytn gcntaytgyy tnytnytngc nttygcnwsn        60
ggnytngtny tnwsnmgngt nccncaygtn cargngnarc arcargartg ggarggnacn      120
gargarytnc cnwsnccncc ngaycaygcn garmgngcng argarcarca ygaraartay      180
mgnccnwsnc argaycargg nytnccngcn wsnmgntgyy tnmgntgytg ygayccnggn      240
acnwsnatgt ayccngcnac ngcngtnccn carathaaya thacnathyt naarggngar      300
aarggngaym gnggngaymg nggnytncar ggnaartayg gnaaracngg nwsngcnggn      360
gcnmgnggnc ayacnggncc naarggncar aarggnwsna tgggngcncc ngngngarmgn      420 tgyaarwsnc aytaygcngc nttywsngtn ggnmgnaara arccnatgca ywsnaaycay      480
taytaycara cngtnathtt ygacnngar ttygtnaayy tntaygayca yttyaayatg       540
ttyacnggna arttytaytg ytaygtnccn ggnytntayt tyttywsnyt naaygtncay      600
acntggaayc araargarac ntayytncay athatgaara aygargarga rgtngtnath      660
ytnttygcnc argtnggnga ymgnwsnath atgcarwsnc arwsnytnat gytngarytn      720
mgngarcarg aycargtntg ggtnmgnytn tayaarggng armgngaraa ygcnathtty      780
wsngargary tngayacnta yathacntty wsnggntayy tngtnaarca ygcnacngar      840 ccn                                                                     843

<210> SEQ ID NO 24
<211> LENGTH: 24
<212> TYPE: DNA
<213> ORGANISM: Artificial Sequence
<220> FEATURE:
<223> OTHER INFORMATION: Oligonucleotide ZC15040

<400> SEQUENCE: 24
actcattcta gactagggct cggt                                               24

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide ZC15033

<400> SEQUENCE: 25
atgaatggat ccctggtcct gagt                                               24

<210> SEQ ID NO 26
<211> LENGTH: 7
<212> TYPE: PRT
<213> ORGANISM: Artificial Sequence
<220> FEATURE:
<223> OTHER INFORMATION: Glu-Glu affinity tag peptide

<400> SEQUENCE: 26

Glu Glu Tyr Met Pro Met Glu
 1               5

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide ZC15721

<400> SEQUENCE: 27
ctgtaggaat tcatgggctc ccgt                                              24

<210> SEQ ID NO 28
<211> LENGTH: 24
<212> TYPE: DNA
<213> ORGANISM: Artificial Sequence
<220> FEATURE:
<223> OTHER INFORMATION: Oligonucleotide ZC15035

<400> SEQUENCE: 28
attcatggat ccgggctcgg tggc                                              24

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide ZC13006

<400> SEQUENCE: 29
ggctgtcctc taagcgtcac                                                   20

<210> SEQ ID NO 30
<211> LENGTH: 19
<212> TYPE: DNA
<213> ORGANISM: Artificial Sequence
<220> FEATURE:
<223> OTHER INFORMATION: Oligonucleotide ZC13007

<400> SEQUENCE: 30 agggtcaca gggatgcca                                                     19

<210> SEQ ID NO 31
<211> LENGTH: 6
<212> TYPE: PRT
<213> ORGANISM: Artificial Sequence
<220> FEATURE:
<223> OTHER INFORMATION: Glu-Glu peptide

<400> SEQUENCE: 31

Gly Tyr Met Pro Val Asp
 1               5

<210> SEQ ID NO 32
<211> LENGTH: 25
<212> TYPE: DNA
<213> ORGANISM: Artificial Sequence -continued

```
<220> FEATURE:
<223> OTHER INFORMATION: Oligonucleotide ZC6768

<400> SEQUENCE: 32
gcaattaacc ctcactaaag ggaac                                          25

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide ZC18297

<400> SEQUENCE: 33
tcctgaaagg cgagaaaggt g                                              21

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide ZC18298

<400> SEQUENCE: 34
ttccctgagt ctgagctagg                                                20

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide ZC18402

<400> SEQUENCE: 35
tccagagtga ctggggaagt g                                              21

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide ZC18403

<400> SEQUENCE: 36
agtgacgagt tcgacaccta c                                              21

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide ZC18456

<400> SEQUENCE: 37
tgtgttccca ttcctggaca c                                              21

<210> SEQ ID NO 38
<211> LENGTH: 21
<212> TYPE: DNA
<213> ORGANISM: Artificial Sequence
<220> FEATURE:
<223> OTHER INFORMATION: Oligonucleotide ZC18457

<400> SEQUENCE: 38
tccttccagc tggctggaaa g                                              21
```

-continued

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide ZC18560

<400> SEQUENCE: 39
agaatgcagg gataggtcag                                              20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide ZC18561

<400> SEQUENCE: 40
tcagaggatc ctgacagcag                                              20

<210> SEQ ID NO 41
<211> LENGTH: 21
<212> TYPE: DNA
<213> ORGANISM: Artificial Sequence
<220> FEATURE:
<223> OTHER INFORMATION: Oligonucleotide ZC18687

<400> SEQUENCE: 41
tggacacgtg agagggactt c                                            21

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide ZC18688

<400> SEQUENCE: 42
agcagtagaa cttcccagtg                                              20

<210> SEQ ID NO 43
<211> LENGTH: 2559
<212> TYPE: DNA
<213> ORGANISM: Mus musculus
<220> FEATURE:
<221> NAME/KEY: CDS
<222> LOCATION: (70)...(912)
<223> OTHER INFORMATION: mouse ortholog

<400> SEQUENCE: 43
gaattcggat cctggaagag atgggattgt tataggcgga aagagagaaa cccagagaag      60 tccaggaag atg ggc tcc tgt gca cag gga ttc atg ctg gga tgc tgc ctg     111
          Met Gly Ser Cys Ala Gln Gly Phe Met Leu Gly Cys Cys Leu
            1               5                  10 ctg ctg gcc atc acc tgg ggc ccc atc ctg agc ctt gtg cca cgc gtt     159
Leu Leu Ala Ile Thr Trp Gly Pro Ile Leu Ser Leu Val Pro Arg Val
 15                  20                  25                  30 cag gag gaa caa cag gag tgg gaa gag aca gag gag ctg cca tct cct     207
Gln Glu Glu Gln Gln Glu Trp Glu Glu Thr Glu Glu Leu Pro Ser Pro
                 35                  40                  45 ctg gat cct gtg aca agg cct gaa gaa aca cga gag aag tat agc cct     255
Leu Asp Pro Val Thr Arg Pro Glu Glu Thr Arg Glu Lys Tyr Ser Pro
             50                  55                  60 cgc cag ggt gag gac ctc ccc act tct cgg tgc tac cga tgc tgt gac     303

-continued

```
                Arg Gln Gly Glu Asp Leu Pro Thr Ser Arg Cys Tyr Arg Cys Cys Asp
                            65                  70                  75 ccc agc aca cct gta tac cag aca att cct cca ccc cag atc aac atc      351
Pro Ser Thr Pro Val Tyr Gln Thr Ile Pro Pro Pro Gln Ile Asn Ile
 80                  85                  90 acc atc ctg aaa ggc gag aaa ggt gac cga ggg gat cga ggc ctc cag      399
Thr Ile Leu Lys Gly Glu Lys Gly Asp Arg Gly Asp Arg Gly Leu Gln
 95                 100                 105                 110 ggg aag tac ggc aaa ata ggt tct aca ggt ccc agg ggc cat gtt ggc      447
Gly Lys Tyr Gly Lys Ile Gly Ser Thr Gly Pro Arg Gly His Val Gly
                115                 120                 125 ccc aaa ggg cag aag gga tcc att gga gcc cct ggg aac cac tgc aag      495
Pro Lys Gly Gln Lys Gly Ser Ile Gly Ala Pro Gly Asn His Cys Lys
                130                 135                 140 agc cag tac gca gcc ttc tcc gtg ggc cgg aag aag gct ttg cac agc      543
Ser Gln Tyr Ala Ala Phe Ser Val Gly Arg Lys Lys Ala Leu His Ser
                145                 150                 155 aac gac tac ttc cag ccc gtg gtc ttc gac acg gag ttt gtg aac ctc      591
Asn Asp Tyr Phe Gln Pro Val Val Phe Asp Thr Glu Phe Val Asn Leu
                160                 165                 170 tac aaa cac ttc aat atg ttc act ggg aag ttc tac tgc tat gtg ccg      639
Tyr Lys His Phe Asn Met Phe Thr Gly Lys Phe Tyr Cys Tyr Val Pro
175                 180                 185                 190 ggc atc tac ttc ttc agc ctc aac gtg cac act tgg aac cag aag gag      687
Gly Ile Tyr Phe Phe Ser Leu Asn Val His Thr Trp Asn Gln Lys Glu
                195                 200                 205 acg tac ctg cac atc atg aag aac gag gag gag gtg gtg atc ctg tat      735
Thr Tyr Leu His Ile Met Lys Asn Glu Glu Glu Val Val Ile Leu Tyr
                210                 215                 220 gcg cag gtg agc gac cgc agc atc atg cag agt cag agc ctg atg atg      783
Ala Gln Val Ser Asp Arg Ser Ile Met Gln Ser Gln Ser Leu Met Met
                225                 230                 235 gag ctg cgg gag gag gat gag gtc tgg gtg cgt ctc ttc aag ggc gag      831
Glu Leu Arg Glu Glu Asp Glu Val Trp Val Arg Leu Phe Lys Gly Glu
240                 245                 250 cgt gag aac gcc att ttc agt gac gag ttc gac acc tac atc acc ttc      879
Arg Glu Asn Ala Ile Phe Ser Asp Glu Phe Asp Thr Tyr Ile Thr Phe
255                 260                 265                 270 agt ggc tac ctg gtc aag cca gcc tct gag ccc tagtggacac tcctgtggag    932
Ser Gly Tyr Leu Val Lys Pro Ala Ser Glu Pro
                275                 280 cttttgtgga ctgctgacct ccttgcctgg caccctgacc tatccctgca ttctacagac    992
actggagtcc tgccccgggc tgaccccatt ttctctctgc tccatcctgg cttccttggc   1052
cttggcttcc aaagttttgg cttttgacaa gatgcccttg ccactgggaa atcccaaagg   1112
atggtgcgat cccagatctg gctgctactc taagcagaga gctgccggca gatgaaatca   1172
ttgggcgggg agcctgtgag gatattgggg ggcctccagc tccttctgtg tacacagcct   1232
tagacgaccc tgtgctgtgt tgtcccgtgg ccacagggtg ttccagagca gcccctgt     1292 gtgttcccat tcctggacac aagtaagcaa atatcatggg tttcttagga acgaagtcaa   1352
gcagaaaaga gaaagaaagg tggtgttagt tttggctttc cagccagctg gaaggaggga   1412
tggggagaga gagagagaga gagctatttg tattggggaa actgaggcat aggaaaaaca   1472
tgaatggcaa cagagtagct gcagtttgtg ggtttggaaa ccacatctga cttaactcta   1532
gatcacatat gagcttttcct ggggacagca ggactgacct ccgagctctg ttgacatgct  1592
atagccttgc ccaggggctg gtcaatcttt ctgagccaca ctagtaaaag ggttggagga   1652
```

-continued

```
gaacagcaag tgcccoctgt ggttggctct gggctggtgg cagcatcctg cttgccccaa    1712
ctcacaggat cctgacagca gctgggaacc tcagggactc ctgcagcttt tctgtaaga    1772 aataaagctc ctactatgtc ccagtacctc tctgctctgc tccacttccc cagtcactct    1832
ggaccccagg gtgggagggc tctcttgcct gttgggacat cagttcccct tcctccttct    1892
tggtgaatta accatggaag gaccagggct cggatttggg ttcccaaact gcccttcacc    1952
atccctagtg tcctgcttcc ttcccagttc agcatcctgt ctgggaactt gatactttaa    2012
cctgctagag cggatgagtc tgatagacct gcccagccct gacacagccc tagtcagctt    2072
atggacacgt gagagggact tcctttgaga cccagagctg gggtagagct ataaaaatct    2132
acctattccc gggtcaaccc caagtggtag aagaggacac aggctatccc gccctagctc    2192
agactcaggg aaggcctcag gcctgattgt ctgactgcag agagcctgtg ttctttcccc    2252
atctcacccc gtgttgatcc ccagggcctg ggccactgga tatctgcttt gtgccaacta    2312
ggccttgctt gctgcttcct ggtggcccctt ggttaggatc cctctcttt ccttctggag    2372 ctcaatgtac gtatatgcca cctccgaagg ggcttctgct ggtcagactc tccaagccac    2432
ttccatgggt gtgcctacag cagaggctgc tgcctcctgt gtctaccct gctctttcca    2492 gaaaacatta aacttgccat ggcgattcac agcaaaaaaa aaaaaaaaaa aaaaaaagg    2552 gcggccg                                                                2559
```

<210> SEQ ID NO 44
<211> LENGTH: 281
<212> TYPE: PRT
<213> ORGANISM: Mus musculus

<400> SEQUENCE: 44

```
Met Gly Ser Cys Ala Gln Gly Phe Met Leu Gly Cys Cys Leu Leu Leu
 1               5                  10                  15

Ala Ile Thr Trp Gly Pro Ile Leu Ser Leu Val Pro Arg Val Gln Glu
             20                  25                  30

Glu Gln Gln Glu Trp Glu Glu Thr Glu Glu Leu Pro Ser Pro Leu Asp
         35                  40                  45

Pro Val Thr Arg Pro Glu Glu Thr Arg Glu Lys Tyr Ser Pro Arg Gln
     50                  55                  60

Gly Glu Asp Leu Pro Thr Ser Arg Cys Tyr Arg Cys Cys Asp Pro Ser
 65                  70                  75                  80

Thr Pro Val Tyr Gln Thr Ile Pro Pro Gln Ile Asn Ile Thr Ile
                 85                  90                  95

Leu Lys Gly Glu Lys Gly Asp Arg Gly Asp Arg Gly Leu Gln Gly Lys
            100                 105                 110

Tyr Gly Lys Ile Gly Ser Thr Gly Pro Arg Gly His Val Gly Pro Lys
        115                 120                 125

Gly Gln Lys Gly Ser Ile Gly Ala Pro Gly Asn His Cys Lys Ser Gln
    130                 135                 140

Tyr Ala Ala Phe Ser Val Gly Arg Lys Lys Ala Leu His Ser Asn Asp
145                 150                 155                 160

Tyr Phe Gln Pro Val Val Phe Asp Thr Glu Phe Val Asn Leu Tyr Lys
                165                 170                 175

His Phe Asn Met Phe Thr Gly Lys Phe Tyr Cys Tyr Val Pro Gly Ile
            180                 185                 190

Tyr Phe Phe Ser Leu Asn Val His Thr Trp Asn Gln Lys Glu Thr Tyr
        195                 200                 205
```

```
Leu His Ile Met Lys Asn Glu Glu Val Val Ile Leu Tyr Ala Gln
    210                 215                 220

Val Ser Asp Arg Ser Ile Met Gln Ser Gln Ser Leu Met Met Glu Leu
225                 230                 235                 240

Arg Glu Glu Asp Glu Val Trp Val Arg Leu Phe Lys Gly Glu Arg Glu
                245                 250                 255

Asn Ala Ile Phe Ser Asp Glu Phe Asp Thr Tyr Ile Thr Phe Ser Gly
            260                 265                 270

Tyr Leu Val Lys Pro Ala Ser Glu Pro
        275                 280

<210> SEQ ID NO 45
<211> LENGTH: 23
<212> TYPE: DNA
<213> ORGANISM: Artificial Sequence
<220> FEATURE:
<223> OTHER INFORMATION: Oligonucleotide ZC23,698

<400> SEQUENCE: 45
gaattcgaat tcctttgttt cca                                      23

<210> SEQ ID NO 46
<211> LENGTH: 43
<212> TYPE: DNA
<213> ORGANISM: Artificial Sequence
<220> FEATURE:
<223> OTHER INFORMATION: Oligonucleotide ZC23,694

<400> SEQUENCE: 46
taatacgact cactataggg aggaggtacc aggtcacag cag                 43

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide ZC23,703

<400> SEQUENCE: 47
tctacgacca cttcaacatg                                          20

<210> SEQ ID NO 48
<211> LENGTH: 22
<212> TYPE: DNA
<213> ORGANISM: Artificial Sequence
<220> FEATURE:
<223> OTHER INFORMATION: Oligonucleotide ZC23,697

<400> SEQUENCE: 48
gtaattgttt attgtccaga tg                                       22

<210> SEQ ID NO 49
<211> LENGTH: 43
<212> TYPE: DNA
<213> ORGANISM: Artificial Sequence
<220> FEATURE:
<223> OTHER INFORMATION: Oligonucleotide ZC24,441

<400> SEQUENCE: 49
atgcattaac cctcactaaa ggggagaggg ctgaagaaca aca                43

<210> SEQ ID NO 50
<211> LENGTH: 41
<212> TYPE: DNA
```

<213> ORGANISM: Artificial Sequence
<220> FEATURE:
<223> OTHER INFORMATION: Oligonucleotide ZC24,442

<400> SEQUENCE: 50
taatacgact cactataggg aggggcggcg tagtggctct t            41

<210> SEQ ID NO 51
<211> LENGTH: 244
<212> TYPE: PRT
<213> ORGANISM: Homo sapiens

<400> SEQUENCE: 51

```
Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
        35                  40                  45

His Asn Gly Ala Pro Gly Arg Asp Gly Arg Asp Gly Thr Pro Gly Glu
    50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125

Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn
```

<210> SEQ ID NO 52
<211> LENGTH: 245
<212> TYPE: PRT
<213> ORGANISM: Homo sapiens

<400> SEQUENCE: 52

```
Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45
```

```
Gly Glu Gln Gly Glu Pro Gly Ala Pro Gly Ile Arg Thr Gly Ile Gln
    50                  55                  60
Gly Leu Lys Gly Asp Gln Gly Glu Pro Gly Pro Ser Gly Asn Pro Gly
 65                  70                  75                  80
Lys Val Gly Tyr Pro Gly Pro Ser Gly Pro Leu Gly Ala Arg Gly Ile
                 85                  90                  95
Pro Gly Ile Lys Gly Thr Lys Gly Ser Pro Gly Asn Ile Lys Asp Gln
                100                 105                 110
Pro Arg Pro Ala Phe Ser Ala Ile Arg Arg Asn Pro Pro Met Gly Gly
            115                 120                 125
Asn Val Val Ile Phe Asp Thr Val Ile Thr Asn Gln Glu Glu Pro Tyr
        130                 135                 140
Gln Asn His Ser Gly Arg Phe Val Cys Thr Val Pro Gly Tyr Tyr Tyr
145                 150                 155                 160
Phe Thr Phe Gln Val Leu Ser Gln Trp Glu Ile Cys Leu Ser Ile Val
                165                 170                 175
Ser Ser Ser Arg Gly Gln Val Arg Arg Ser Leu Gly Phe Cys Asp Thr
                180                 185                 190
Thr Asn Lys Gly Leu Phe Gln Val Val Ser Gly Gly Met Val Leu Gln
            195                 200                 205
Leu Gln Gln Gly Asp Gln Val Trp Val Glu Lys Asp Pro Lys Lys Gly
        210                 215                 220
His Ile Tyr Gln Gly Ser Glu Ala Asp Ser Val Phe Ser Gly Phe Leu
225                 230                 235                 240
Ile Phe Pro Ser Ala
                245

<210> SEQ ID NO 53
<211> LENGTH: 215
<212> TYPE: PRT
<213> ORGANISM: Tamias sibricus

<400> SEQUENCE: 53

Met Pro Ala Gln Arg Gly Gly Ala Leu Ser Met Gly Ala Ala Gly Phe
  1               5                  10                  15
Trp Ile Leu Val Leu Ser Ile Thr Ser Ala Leu Ala Asp Ser Asn Asn
                 20                  25                  30
Gln Gly Asn Ser Glu Pro Cys Gly Pro Pro Gly Pro Pro Gly Pro Pro
             35                  40                  45
Gly Ile Pro Gly Phe Pro Gly Ala Pro Gly Ala Leu Gly Pro Pro Gly
         50                  55                  60
Pro Pro Gly Val Pro Gly Ile Pro Gly Pro Gln Gly Pro Pro Gly Asp
 65                  70                  75                  80
Val Glu Lys Cys Ser Ser Arg Pro Lys Ser Ala Phe Ala Val Lys Leu
                 85                  90                  95
Ser Glu Arg Pro Pro Glu Pro Phe Gln Pro Ile Val Phe Lys Glu Ala
                100                 105                 110
Leu Tyr Asn Gln Glu Gly His Phe Asn Met Ala Thr Gly Glu Phe Ser
            115                 120                 125
Cys Val Leu Pro Gly Val Tyr Asn Phe Gly Phe Asp Ile Arg Leu Phe
        130                 135                 140
Gln Ser Ser Val Lys Ile Arg Leu Met Arg Asp Gly Ile Gln Val Arg
145                 150                 155                 160
Glu Lys Glu Ala Gln Ala Asn Asp Ser Tyr Lys His Ala Met Gly Ser
```

165                 170                 175
Val Ile Met Ala Leu Gly Lys Gly Asp Lys Val Trp Leu Glu Ser Lys
                  180                 185                 190

Leu Lys Gly Thr Glu Ser Glu Lys Gly Ile Thr His Ile Val Phe Phe
              195                 200                 205

Gly Tyr Leu Leu Tyr Gly Lys
          210                 215

<210> SEQ ID NO 54
<211> LENGTH: 215
<212> TYPE: PRT
<213> ORGANISM: Tamias sibricus

<400> SEQUENCE: 54

Met Tyr Glu Ala Gly Lys Arg Ala Ser Phe Met Gly Gly Ala Gly Ile
  1               5                  10                  15

Trp Ile Leu Ala Leu Ser Val Leu Met His Val Val Cys Ser Glu Thr
                 20                  25                  30

Gln Gly Asn Pro Glu Ser Cys Asn Val Pro Gly Pro Gln Gly Pro Pro
             35                  40                  45

Gly Met Arg Gly Pro Pro Gly Thr Pro Gly Lys Pro Gly Pro Pro Gly
         50                  55                  60

Trp Asn Gly Phe Pro Gly Leu Pro Gly Pro Pro Gly Pro Pro Gly Met
65                  70                  75                  80

Thr Val Asn Cys His Ser Lys Gly Thr Ser Ala Phe Ala Val Lys Ala
                 85                  90                  95

Asn Glu Leu Pro Pro Ala Pro Ser Gln Pro Val Ile Phe Lys Glu Ala
            100                 105                 110

Leu His Asp Ala Gln Gly His Phe Asp Leu Ala Thr Gly Val Phe Thr
        115                 120                 125

Cys Pro Val Pro Gly Leu Tyr Gln Phe Gly Phe His Ile Glu Ala Val
    130                 135                 140

Gln Arg Ala Val Lys Val Ser Leu Met Arg Asn Gly Thr Gln Val Met
145                 150                 155                 160

Glu Arg Glu Ala Glu Ala Gln Asp Gly Tyr Glu His Ile Ser Gly Thr
                165                 170                 175

Ala Ile Leu Gln Leu Gly Met Glu Asp Arg Val Trp Leu Glu Asn Lys
            180                 185                 190

Leu Ser Gln Thr Asp Leu Glu Arg Gly Thr Val Gln Ala Val Phe Ser
        195                 200                 205

Gly Phe Leu Ile His Glu Asn
    210                 215

<210> SEQ ID NO 55
<211> LENGTH: 224
<212> TYPE: PRT
<213> ORGANISM: Rattus norvegicus

<400> SEQUENCE: 55

Met Pro Ala Pro Gly Arg Gly Pro Arg Gly Pro Leu Leu Ser Met Pro
  1               5                  10                  15

Gly Arg Arg Gly Ala Leu Arg Glu Pro Ala Asp Phe Gly Ser Ser Leu
                 20                  25                  30

Gly Ala Ala Leu Ala Leu Leu Leu Leu Pro Ala Cys Cys Pro
             35                  40                  45

Val Lys Ala Gln Asn Asp Thr Glu Pro Ile Val Leu Glu Gly Lys Cys

-continued

```
                50                          55                          60
Leu Val Val Cys Asp Ser Ser Pro Ser Gly Asp Gly Ala Val Thr Ser
 65                  70                      75                      80

Ser Leu Gly Ile Ser Val Arg Ser Gly Ser Ala Lys Val Ala Phe Ser
                 85                      90                      95

Ala Thr Arg Ser Thr Asn His Glu Pro Ser Glu Met Ser Asn Arg Thr
            100                     105                 110

Met Thr Ile Tyr Phe Asp Gln Val Leu Val Asn Ile Gly Asn His Phe
        115                     120                 125

Asp Leu Ala Ser Ser Ile Phe Val Ala Pro Arg Lys Gly Ile Tyr Ser
    130                 135                     140

Phe Ser Phe His Val Val Lys Val Tyr Asn Arg Gln Thr Ile Gln Val
145                 150                     155                 160

Ser Leu Met Gln Asn Gly Tyr Pro Val Ile Ser Ala Phe Ala Gly Asp
                165                     170                 175

Gln Asp Val Thr Arg Glu Ala Ala Ser Asn Gly Val Leu Leu Leu Met
            180                 185                 190

Glu Arg Glu Asp Lys Val His Leu Lys Leu Glu Arg Gly Asn Leu Met
        195                 200                 205

Gly Gly Trp Lys Tyr Ser Thr Phe Ser Gly Phe Leu Val Phe Pro Leu
    210                 215                 220
```